US007105652B2

(12) United States Patent
Callaghan et al.

(10) Patent No.: US 7,105,652 B2
(45) Date of Patent: Sep. 12, 2006

(54) HUMAN TUMOR SUPPRESSOR GENE

(75) Inventors: Michelle J. Callaghan, Drummoyne (AU); Robert L. Sutherland, Lindfield (AU); Colin K. Watts, Avalon (AU)

(73) Assignee: Garvan Institute of Medical Research, Darlinghurst (AU)

( * ) Notice: Subject to any disclaimer, the term of this patent is extended or adjusted under 35 U.S.C. 154(b) by 298 days.

(21) Appl. No.: 10/151,736

(22) Filed: May 16, 2002

(65) Prior Publication Data

US 2002/0192160 A1 Dec. 19, 2002

Related U.S. Application Data

(63) Continuation of application No. 09/403,402, filed as application No. PCT/AU98/00280 on Apr. 20, 1998, now abandoned.

(30) Foreign Application Priority Data

Apr. 21, 1997 (AU) .................................... PO6334

(51) Int. Cl.
*C07H 21/04* (2006.01)
*C01N 5/00* (2006.01)
*C01N 15/63* (2006.01)
*C01Q 1/68* (2006.01)
*C01P 21/06* (2006.01)

(52) U.S. Cl. .................. 536/23.5; 536/23.1; 536/23.4; 435/6; 435/69.1; 435/320.1; 435/325; 435/455

(58) Field of Classification Search ............... 536/23.1, 536/23.4, 23.5
See application file for complete search history.

(56) References Cited

FOREIGN PATENT DOCUMENTS

WO 9715674 5/1997

OTHER PUBLICATIONS

Wan et al. Molecular Endocrinology 16:1204-1214, 2002.*
Henderson, J. Biological Chemistry, vol. 277, No. 29, pp. 26468-26478, 2002.*
Ngo et al., in The protein Folding problem and -tertiary Structure prediction, 1994, Merz et al., (ed.), Birkhauser, Boston, MA, pp. 432-506, 1994.*
Yamao, F, J. of Biochemistry, vol. 125, 2:223-229, Feb. 1999.*
Clancy et al. EDD, the human orthologue of the hyperplastic discs tumour suppressor gene, is amplified and overexpressed in cancer. Oncogene.22(32):5070-81, 2003.*
Rudinger J in Peptide Hormones. Editor Parsons JA. pp. 1-7, 1976, Unversity Park Press, Baltimore.*
Wolff RK (Drug Development Research 41:129-141, 1997.*
Muller et al (Accession No. X64411.1, database GenEmbl, Oct. 23, 1992.*
Callaghan MJ et al. Oncogene 17:3479-3491, 1998.*
Cameron ER. Molecular Biotechnology 7:253-265, 1997.*
Mullins JJ et al. Hypertension 22:630-633, 1993.*
Callaghan et al., "*EDD (M-19): Product SC-9562*", Santa Cruz Biotechnology, Inc. (Apr. 2001).
Callaghan et al., "*EDD (N-19):Product SC-9561*", Santa Cruz Biotechnology, Inc. (Apr. 2001).
Huibregtse et al., "*The Large Subunit of RNA Polymerase II is A substrate of the Rsp5 Ubiquitin-Protein Ligase*", Proc. Natl Acad Sci. 94: 3656-3661 (1997).
Hatakeyama et al., "*Subcellular Localization and Ubiquitin-Conjugating Enzyme (E2) Interactions of Mammalian HECT Family Ubiquitin Protein Ligases*", The Journal of Biol. Chemistry vol. 272: 15805-15092 (1997).
Müller et al, *Nucleic Acids Research*, 20:7, pp. 1471-1475 (1992).
Mansfield et al., *Developmental Biology*, 165, pp. 507-526 (1994).
Jon M. Huibretgtse et al., "*A Family of Proteins Structurally and Functionally Related to the E6-AP Ubiquitin-Protein Ligase*" Proc. Natl Acad Sci vol. 92, pp. 2563-2567 (Mar. 1995).

* cited by examiner

*Primary Examiner*—Sumesh Kaushal
(74) *Attorney, Agent, or Firm*—Carol L. Francis; Bozicevic, Field & Francis LLP

(57) ABSTRACT

A novel human progestin-regulated gene designated EDD ( E3 isolated by Differential Display) is disclosed which encodes a product exhibiting significant amino acid sequence identity with the HYD protein (hyperplastic discs) from *Drosophila melanogaster* and the 100 kDa HECT ( homologous to E6-AP carboxyl terminus) domain protein from rat. The EDD gene appears to represent a tumour suppressor gene and the detection of a polymorphism or alteration in the gene from a subject may be useful for the diagnosis or determination of a predisposition to hyperproliferative disease such as a cancer. An assay for assessing progestin-responsiveness in a subject is also disclosed.

9 Claims, 11 Drawing Sheets

Figure 1A:
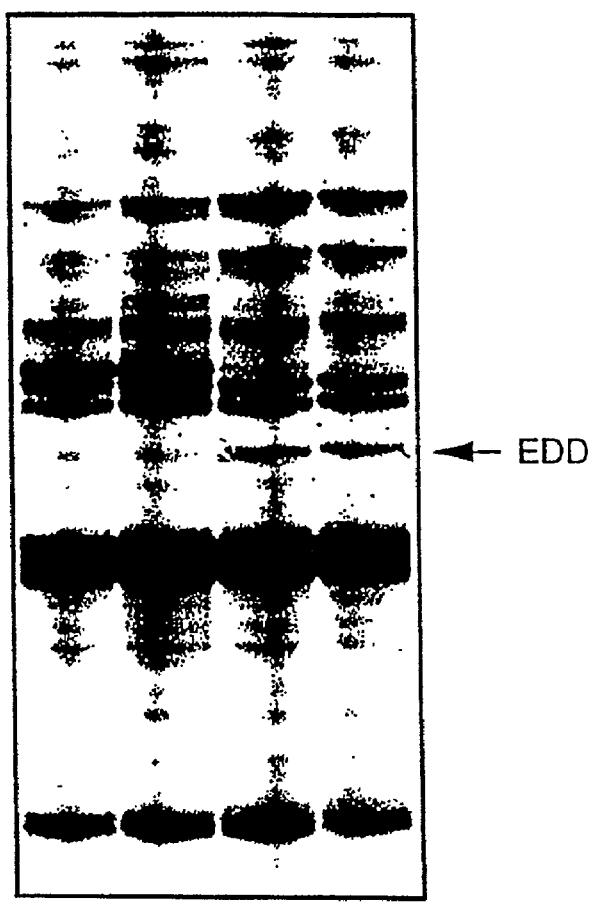

CONTROL
ACTINOMYCIN
ORG 2058
ACT + ORG 2058

↑ EDD

CONTROL
CHX
CHX + ORG 2058
ORG 2058

↑ EDD

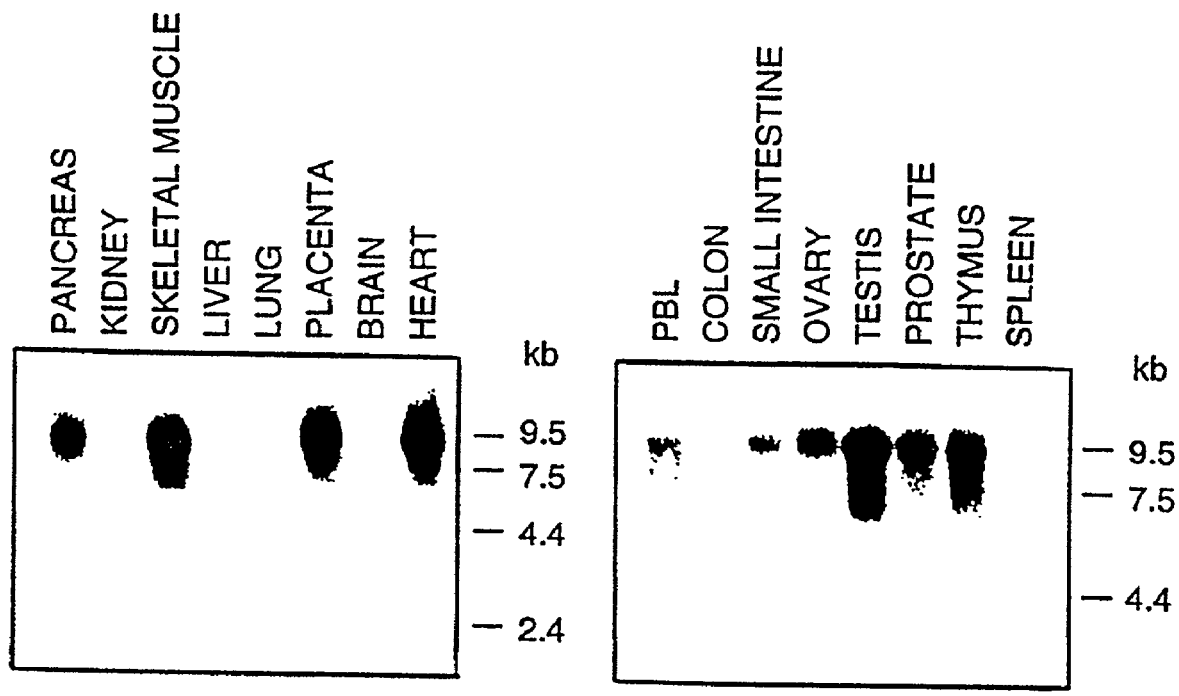
FIGURE 2A
FIGURE 2B
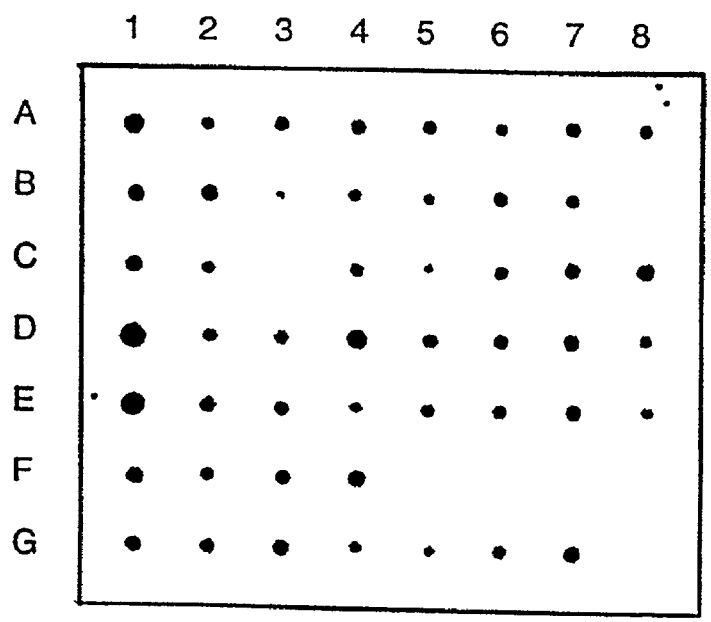

FIGURE 3B

```
   1 CGCCCTCGAG TGGAGGACGA GAAGGAAAGC ACCATGACGT CCATCCATTT CGTGGTTCAC
  61 CCGCTGCCGG GCACCGAGGA CCAGCTCAAT GACAGGTTAC GAGAAGTTTC TGAGAAGCTG
 121 AACAAATATA ATTTAAACAG CCACCCCCCT TTGAATGTAT TCCAACAGGC TACTATTAAA
 181 CAGTGTGTGG TGGGACCAAA TCATGCTGCC TTTCTTCTTG AGGATGGTAG AGTTTGCAGG
 241 ATTGGTTTTT CAGTACAGCC AGACAGATTG GAATTGGGTA AACCTGATAA TAATGATGGG
 301 TCAAAGTTGA ACAGCAACTC GGGGGCAGGG AGGACGTCAA GGCCTGGTAG GACAAGCGAC
 361 TCTCCATGGT TTCTCTCAGG TTCTGAGACT CTAGGCAGGC TGGCAGGCAA CACCTTAGGA
 421 AGCCGCTGGA GTTCTGGAGT GGGTGGAAGT GGTGGAGGAT CCTCTGGTAG GTCATCAGCT
 481 GGAGCTCGAG ATTCCCGCCG GCAGACTCGA GTTATTCGGA CAGGACGGGA TCGAGGGTCT
 541 GGGCTTTTGG GCAGTCAGCC CCAGCCAGTT ATTCCAGCAT CTGTCATTCC AGAGGAGCTG
 601 ATTTCACAGG CCCAAGTTGT TTTACAAGGC AAATCCAGAA GTGTCATTAT TCGAGAACTT
 661 CAGAGAACAA ATCTTGATGT GAACCTTGCT GTAAATAATT TACTTAGCCG GGATGATGAA
 721 GATGGAGATG ATGGGGATGA TACAGCCAGC GAATCTTATT GGCTGGAGA GGATCTTATG
 781 TCTCTCCTTG ATGCCGACAT TCATTCTGCC CACCCAAGTG TCATTATTGA TGCAGATGCC
 841 ATGTTTTCTG AAGACATTAG CTATTTTGGT TACCCTTCTT TTCGTCGTTC ATCACTTTCC
 901 AGGCTAGGCT CATCTCGAGT TCTCCTTCTT CCCTTAGAGA GAGACTCTGA GCTGTTGCGT
 961 GAACGCGAAT CCGTTTTACG TTTACGTGAA CGAAGGTGGC TTGATGGAGC CTCATTTGAT
1021 AATGAAAGGG GTTCTACCAA GCAAGGAAGG AGAGCCAAAC TTGATAAGAA GAATACACCT
1081 GTTCAAAGTC CAGTATCTCT AGGAGAAGAT TTGCAGTGGT GGCCTGATAA GGATGGAACA
1141 AAATTCATCT GTATGGCTCT GTATTCTGAA CTTCTGGCTG TCAGCAGTAA AGGAGAACTT
1201 TATCAGTGGA AATGGAGTGA ATCTGAGCCT TACAGAAATG CCCAGAATCC TTCATTACAT
1261 CATCCACGAG CAACATTTTT GGGGTTAACC AATGAAAAGA TAGTCCTCCT GTCTGCAAAT
1321 AGCATAAGAG CAACTGTAGC TACAGAAAAG AACAAGGTTG CTACATGGGT GGATGAAACT
1381 TTAAGTTCTG TGGCTTCTAA ATTAGAGCAC ACTGCTCAGA CTTACTCTGA ACTTCAAGGA
1441 GAGCGGATAG TTTCTTTACA TTGCTGTGCC CTTTACACCT GCGCTCAGCT GGAAAACAGT
1501 TTATATTGGT GGGGTGTAGT TCCTTTTAGT CAAAGGAAGA AAATGTTAGA GAAAGCTAGA
1561 GCAAAAAATA AAAGCCTAA ATCCAGTGCT GGTATTTCTT CAATGCCGAA CATCACTGTT
1621 GGTACCCAGG TATGCTTGAG AAATAATCCT CTTTATCATG CTGGAGCAGT TGCATTTTCA
1681 ATTAGTGCTG GGATTCCTAA AGTTGGTGTC TTAATGGAGT CAGTTTGGAA TATGAATGAC
1741 AGCTGTAGAT TCAACTTAG ATCTCCTGAA AGCTTGAAAA ACATGGAAAA AGCTAGCAAA
1801 ACTACTGAAG CTAAGCCTGA AAGTAAGCAG GAGCCAGTGA AAACAGAAAT GGGTCCTCCA
1861 CCATCTCCAG CATCCACGTG TAGTGATGCA TCCTCAATTG CCAGCAGTGC ATCAATGCCA
1921 TACAAACGAC GACGGTCAAC CCCTGCACCA AAAGAAGAGG AAAAGGTGAA TGAAGAGCAG
1981 TGGTCTCTTC GGGAAGTGGT TTTTGTGGAA GATGTCAAGA ATGTTCCTGT GGCAAGGTG
2041 CTAAAAGTAG ATGGTGCCTA TGTTGCTGTA AAATTTCCAG GAACCTCCAG TAATACTAAC
2101 TGTCAGAACA GCTCTGGTCC AGATGCTGAC CCTTCTTCTC TCCTGCAGGA TTGTAGGTTA
2161 CTTAGAATTG ATGAATTGCA GGTTGTCAAA ACTGGTGGAA CACCGAAGGT TCCCGACTGT
2221 TTCCAAAGGA CTCCTAAAAA GCTTTGTATA CCTGAAAAAA CAGAAATATT AGCAGTGAAT
2281 GTAGATTCCA AAGGTGTTCA TGCTGTTCTG AAGACTGGAA ATTGGGTGCG ATACTGTATC
2341 TTTGATCTTG CTACAGGAAA AGCAGAACAG GAAAATAATT TTCCTACAAG CAGCATTGCT
2401 TTCCTTGGTC AGAATGAGAG GAATGTAGCC ATTTTCACTG CTGGACAGGA ATCTCCCATT
2461 ATTCTTCGAG ATGGAAATGG TACCATCTAC CCAATGGCCA AAGATTGCAT GGGAGGAATA
2521 AGGGATCCCG ATTGGCTGGA TCTTCCACCT ATTAGTAGTC TTGGAATGGG TGTGCATTCT
2581 TTAATAAATC TTCCTGCCAA TTCAACAATC AAAAAGAAAG CTGCTGTTAT CATCATGGCT
2641 GTAGAGAAAC AAACCTTAAT GCAACACATT CTGCGCTGTG ACTATGAGGC CTGTCGACAA
2701 TATCTAATGA ATCTTGAGCA ACGGTTTTTA GAGCAGAATC TACAGATGCT GCAGACATTC
2761 ATCAGCCACA GATGTGATGG AAATCGAAAT ATTTTGCATG CTTGTGTATC AGTTTGCTTT
2821 CCAACCAGCA ATAAAGAAAC TAAAGAAGAA GAGGAAGCGG AGCGTTCTGA AAGAAATACA
2881 TTTGCAGAAA GGCTTTCTGC TGTTGAGGCC ATTGCAAATG CAATATCAGT TGTTTCAAGT
2941 AATGGCCCAG GTAATCGGGC TGGATCATCA AGTAGCCGAA GTTTGAGATT ACGGGAAATG
3001 ATGAGACGTT CGTTGAGAGC AGCTGGTTTG GGTAGACATG AAGCTGGAGC TTCATCCAGT
3061 GACCACCAGG ATCCAGTTTC ACCCCCCATA GCTCCCCCTA GTTGGGTTCC TGACCCTCCT
3121 GCGATGGATC CTGATGGTGA CATTGATTTT ATCCTGGCCC CCGCTGTGGG ATCTCTTACC
3181 ACAGCAGCAA CCGGTACTGG TCAAGGACCA AGCACCTCCA CTATTCCAGG TCCTTCCACA
3241 GAGCCATCTG TAGTAGAATC CAAGGATCGA AAGGCGAATG CTCATTTTAT ATTGAAATTG
3301 TTATGTGACA GTGTGGTTCT CCAGCCCTAT CTACGAGAAC TTCTTTCTGC CAAGGATGCA
3361 AGAGGGATGA CCCCATTTAT GTCAGCTGTA AGTGGCCGAG CTTATCCTGC TGCAATTACC
3421 ATCTTAGAAA CTGCTCAGAA AATTGCAAAA GCTGAAATAT CCTCAAGTGA AAAAGAGGAA
```

FIGURE 3B CONTINUED

```
3481 GATGTATTCA TGGGAATGGT TTGCCCATCA GGTACCAACC CTGATGACTC TCCTTTATAT
3541 GTTTTATGTT GTAATGACAC TTGCAGTTTT ACATGGACTG GAGCAGAGCA CATTAACCAG
3601 GATATTTTTG AGTGTCGAAC TTGTGGCTTG CTGGAGTCAC TGTGTTGTTG TACGGAATGT
3661 GCAGGGGTTT GTCATAAAGG TCATGATTGG AAACTCAAAC GGACATCACC AACAGCCTAC
3721 TGTGACTGTT GGGAGAAATG TAAATGTAAA ACTCTTATTG CTGGACAGAA ATCTGCTCGT
3781 CTTGATCTAC TTTATCGCCT GCTCACTGCT ACTAATCTGG TTACTCTGCC AAACAGCAGG
3841 GGAGAGCACC TCTTACTATT CTTAGTACAG ACAGTCGCAA GGCAGACGGT GGAGCATTGT
3901 CAATACAGGC CACCTCGAAT CAGGGAAGAT CGTAACCGAA AAACAGCCAG TCCTGAAGAT
3961 TCAGATATGC CAGATCATGA TTTAGAGCCT CCAAGATTTG CCCAGCTTGC ATTGGAGCGT
4021 GTTCTACAGG ACTGGAATGC CTTGAAATCT ATGATTATGT TTGGGTCGCA GGAGAATAAA
4081 GACCCTCTTA GTGCCAGCAG TAGAATAGGC CATCTTTTGC CAGAAGAGCA AGTATACCTC
4141 AATCAGCAAA GTGGCACAAT TCGGCTGGAC TGTTTCACTC ATTGCCTTAT AGTTAAGTGT
4201 ACAGCAGATA TTTTGCTTTT AGATACTCTA CTAGGTACAC TAGTGAAAGA ACTCCAAAAC
4261 AAATATACAC CTGGACGTAG AGAAGAAGCT ATTGCTGTGA CAATGAGGTT TCTACGTTCA
4321 GTGGCAAGAG TTTTTGTTAT TCTGAGTGTG GAAATGGCTT CATCCAAAAA GAAAACAAC
4381 TTTATTCCAC AGCCAATTGG AAAATGCAAG CGTGTATTCC AAGCATTGCT ACCTTACGCT
4441 GTGGAAGAAT TGTCCAACGT AGCAGAGTCA CTGATTGTTC CTGTCAGAAT GGGGATTGCT
4501 CGTCCAACTG CACCATTTAC CCTGGCTAGT ACTAGCATAG ATGCCATGCA GGGCAGTGAA
4561 GAATTATTTT CAGTGGAACC ACTGCCACCA CGACCATCAT CTGATCAGTC TAGCAGCTCC
4621 AGTCAGTCTC AGTCATCCTA CATCATCAGG AATCCACAGC AGAGGCGCAT CAGCCAGTCA
4681 CAGCCCGTTC GGGGCAGAGA TGAAGAACAG GATGATATTG TTTCAGCAGA TGTGGAAGAG
4741 GTTGAGGTGG TGGAGGGTGT GGCTGGAGAA GAGGATCATC ATGATGAACA GGAAGAACAC
4801 GGGGAAGAAA ATGCTGAGGC AGAGGGACAA CATGATGAGC ATGATGAAGA CGGGAGTGAT
4861 ATGGAGCTGG ACTTGTTAGC AGCAGCAGAA ACAGAAAGTG ATAGTGAAAG TAACCACAGC
4921 AACCAAGATA ATGCTAGTGG GCGCAGAAGC GTTGTCACTG CAGCAACTGC TGGTTCAGAA
4981 GCAGGAGCAA GCAGTGTTCC TGCCTTCTTT TCTGAAGATG ATTCTCAATC GAATGACTCA
5041 AGTGATTCTG ATAGCAGTAG TAGTCAGAGT GACGACATAG AACAGGAGAC CTTTATGCTT
5101 GATGAGCCAT TAGAAAGAAC CACAAATAGC TCCCATGCCA ATGGTGCTGC CCAAGCTCCC
5161 CGTTCAATGC AGTGGGCTGT CCGCAACACC CTGCATCAGC GAGCAGCCAG TACAGCCCCT
5221 TCCAGTACAT CTACACCAGC AGCAAGTTCA GCGGGTTTGA TTTATATTGA TCCTTCAAAC
5281 TTACGCCGGA GTGGTACCAT CAGTACAAGT GCTGCAGCTG CAGCAGCTGC TTTGGAAGCT
5341 AGCAACGCCA GCAGTTACCT AACATCTGCA AGCAGTTTAG CCAGGGCTTA CAGCATGTCA
5401 TTAGACAAAT CATCGGACTT GATGGGCCTT ATTCCTAAGT ATAATCACCT AGTATACTCT
5461 CAGATTCCAG CAGCTGTGAA ATTGACTTAC CAAGATGCAG TAAACTTACA GAACTATGTA
5521 GAAGAAAAGC TTATTCCCAC TTGGAACTGG ATGGTCAGTA TTATGGATTC TACTGAAGCT
5581 CAATTACGTT ATGGTTCTGC ATTAGCATCT GCTGGTGATC CTGGACATCC AAATCATCCT
5641 CTTCACGCTT CTCAGAATTC AGCGAGAAGA GAGAGGATGA CTGCGCGAGA AGAAGCTAGC
5701 TTACGAACAC TTGAAGGCAG ACGACGTGCC ACCTTGCTTA GCGCCCGTCA AGGAATGATG
5761 TCTGCACGAG GAGACTTCCT AAATTATGCT CTGTCTCTAA TGCGGTCTCA TAATGATGAG
5821 CATTCTGATG TTCTTCCAGT TTTGGATGTT TGCTCATTGA AGCATGTGGC ATATGTTTTT
5881 CAAGCACTTA TATACTGGAT TAAGGCAATG AATCAGCAGA CAACATTGGA TACACCTCAA
5941 CTAGAACGCA AAAGGACGCG AGAACTGGGA GAACTGGGTA TTGATAATGA AGATTCAGAA
6001 CATGAAAATG ATGATGACAC CAATCAAAGT GCTACTTTGA ATGATAAGGA TGATGACTCT
6061 CTTCCTGCAG AAACTGGCCA AAACCATCCA TTTTTCCGAC GTTCAGACTC CATGACATTC
6121 CTTGGGTGTA TACCCCCAAA TCCATTTGAA GTGCCTCTGG CTGAAGCCAT CCCCTTGGCT
6181 GATCAGCCAC ATCTGTTGCA GCCAAATGCT AGAAAGGAGG ATCTTTTTGG CCGTCCAAGT
6241 CAGGGTCTTT ATTCTTCATC TGCCAGTAGT GGGAAATGTT TAATGGAGGT TACAGTGGAT
6301 AGAAACTGCC TAGAGGTTCT TCCAACAAAA ATGTCTTATG CTGCCAATCT GAAAATGTA
6361 ATGAACATGC AAAACCGGCA AAAAAGAAG GGGAAGGAAC AGCCCGTGCT GCCAGAAGAA
6421 ACTGAGAGTT CAAAACCAGG GCCATCTGCT CATGATCTTG CTGCACAATT AAAAGTAGC
6481 TTACTAGCAG AAATAGGACT TACTGAAAGT GAAGGGCCAC CTCTCACATC TTTCAGGCCA
6541 CAGTGTAGCT TTATGGGAAT GGTTCTTTCC CATGATATGC TGCTAGGACG TTGGCGCCTT
6601 TCTTTAGAAC TGTTCGGCAG GGTATTCATG GAAGATGTTG GAGCAGAACC TGGATCAATC
6661 CTAACTGAAT TGGGTGGTTT TGAGGTAAAA GAATCGAAAT TCCGCAGAGA AATGGAAAAA
6721 CTGAGAAACC AGCAGTCAAG AGATTTGTCA CTAGAGGTTG ATCGGGATCG AGATCTTCTC
6781 ATTCAGCAGA CTATGAGGCA GCTTAACAAT CACTTTGGTC GAAGATGTGC TACTATACCA
```

FIGURE 3B CONTINUED

```
6841 ATGGCTGTAC ACAGAGTAAA AGTCACATTT AAGGATGAGC CAGGAGAGGG CAGTGGTGTA
6901 GCACGAAGTT TTTATACAGC CATTGCACAA GCATTTTTAT CAAATGAAAA ATTGCCAAAT
6961 CTAGAGTGTA TCCAAAATGC CAACAAAGGC ACGCACACAA GTTTAATGCA GAGATTAAGG
7021 AACCGAGGAG AGAGAGACCG GGAAAGGGAG AGAGAAAGGG AAATGAGGAG GAGTAGTGGT
7081 TTGCGAGCAG GTTCTCGGAG GGACCGGGAT AGAGACTTTA GAAGACAGCT TTCCATCGAC
7141 ACTAGGCCCT TTAGACCAGC CTCTGAAGGG AATCCTAGCG ATGATCCTGA GCCTTTGCCA
7201 GCACATCGGC AGGCACTTGG AGAGAGGCTT TATCCTCGTG TACAAGCAAT GCAACCAGCA
7261 TTTGCAAGTA AAATCACTGG CATGTTGTTG GATTATCCCA GCTCAGCTGC TTCTCTTCTA
7321 GCAAGTGAGG ATTCTCTGAG AGCAAGAGTG GATGAGGCCA TGGAACTCAT TATTGCACAT
7381 GGACGGGAAA ATGGAGCTGA TAGTATCCTG GATCTTGGAT TAGTAGACTC CTCAGAAAAG
7441 GTACAGCAGG AAAACCGAAA GCGCCATGGC TCTAGTCGAA GTGTAGTAGA TATGGATTTA
7501 GATGATACAG ATGATGGTGA TGACAATGCC CCTTTGTTTT ACCAACCTGG GAAAGAGGA
7561 TTTTATACTC CAAGGCCTGG CAAGAACACA GAAGCAAGGT TGAATTGTTT CAGAAACATT
7621 GGCAGGATTC TTGGACTATG TCTGTTACAG AATGAACTCT GTCCTATCAC ATTGAATAGA
7681 CATGTAATTA AGTATTGCT TGGTAGAAAA GTCAATTGGC ATGATTTTGC TTTTTTTGAT
7741 CCTGTAATGT ATGAGAGTTT GCGGCAACTA ATCCTCGCGT CTCAGAGTTC AGATGCTGAT
7801 GCTGTTTTCT CAGCAATGGA TTTGGCATTT GCAATTGACC TGTGTAAAGA AGAAGGTGGA
7861 GGACAGGTTG AACTCATTCC TAATGGTGTA AAGAGACCAG TCACTCCACA GAATGTATAT
7921 GAGTATGTGC GGAAAGACGC AGAACACAGA ATGTTGGTAG TTGCAGAACA GCCCTTACAT
7981 GCAATGAGGA AAGGTCTACT AGATGTGCTT CCAAAAAATT CATTAGAAGA TTTAACGGCA
8041 GAAGATTTTA GGCTTTTGGT AAATGGCTGC GGTGAAGTCA ATGTGCAAAT GCTGATCAGT
8101 TTTACCTCTT TCAATGATGA ATCAGGAGAA AATGCTGAGA AGCTTCTGCA GTTCAAGCGT
8161 TGGTTCTGGT CAATAGTAGA GAAGATGAGC ATGACAGAAC GACAAGATCT TGTTTACTTT
8221 TGGACATCAA GCCCATCACT GCCAGCCAGT GAAGAAGGAT TCCAGCCTAT GCCCTCAATC
8281 ACAATAAGAC CACCAGATGA CCAACATCTT CCTACTGCAA ATACTTGCAT TTCTCGACTT
8341 TACGTCCCAC TCTATTCCTC TAAACAGATT CTCAAACAGA AATTGTTACT CGCCATTAAG
8401 ACCAAGAATT TTGGTTTTGT GTAGAGTATA AAAAGTGTGT ATTGCTGTGT AATATTACTA
8461 GCAAATTTTG TAGATTTTTT TCCATTTGTC TAT
```

FIGURE 3C

```
   1    MTSIHFVVHP  LPGTEDQLND  RLREVSEKLN  KYNLNSHPPL  NVLEQATIKQ  CVVGPNHAAF
  61    LLEDGRVCRI  GFSVQPDRLE  LGKPDNNDGS  KLNSNSGAGR  TSRPGRTSDS  PWFLSGSETL
 121    GRLAGNTLGS  RWSSGVGGSG  GGSSGRSSAG  ARDSRRQTRV  IRTGRDRGSG  LLGSQPQPVI
 181    PASVIPEELI  SQAQVVLQGK  SRSVIIRELQ  RTNLDVNLAV  NNLLSRDDED  GDDGDDTASE
 241    SYLAGEDLMS  LLDADIHSAH  PSVIIDADAM  FSEDISYFGY  PSFRRSSLSR  LGSSRVLLLP
 301    LERDSELLRE  RESVLRLRER  RWLDGASFDN  ERGSTSKEGE  PNLDKKNTPV  QSPVSLGEDL
 361    QWWPDKDGTK  FICIGALYSE  LLAVSSKGEL  YQWKWSESEP  YRNAQNPSLH  HPRATFLGLT
 421    NEKIVLLSAN  SIRATVATEN  NKVATWVDET  LSSVASKLEH  TAQTYSELQG  ERIVSLHCCA
 481    LYTCAQLENS  LYWWGVVPFS  QRKKMLEKAR  AKNKKPKSSA  GISSMPNITV  GTQVCLRNNP
 541    LYHAGAVAFS  ISAGIPKVGV  LMESVWNMND  SCRFQLRSPE  SLKNMEKASK  TTEAKPESKQ
 601    EPVKTEMGPP  PSPASTCSDA  SSIASSASMP  YKRRRSTPAP  KEEEKVNEEQ  WSLREVVFVE
 661    DVKNVPVGKV  LKVDGAYVAV  KFPGTSSNTN  CQNSSGPDAD  PSSLLQDCRL  LRIDELQVVK
 721    TGGTPKVPDC  FQRTPKKLCI  PEKTEILAVN  VDSKGVHAVL  KTGNWVRYCI  FDLATGKAEQ
 781    ENNFPTSSIA  FLGQNERNVA  IFTAGQESPI  ILRDGNGTIY  PMAKDCMGGI  RDPDWLDLPP
 841    ISSLGMGVHS  LINLPANSTI  KKKAAVIIMA  VEKQTLMQHI  LRCDYEACRQ  YLMNLEQAVV
 901    LEQNLQMLQT  FISHRCDGNR  NILHACVSVC  FPTSNKETKE  EEEAERSERN  TFAERLSAVE
 961    AIANAISVVS  SNGPGNRAGS  SSSRSLRLRE  MMRRSLRAAG  LGRHEAGASS  SDHQDPVSPP
1021    IAPPSWVPDP  PAMDPDGDID  FILAPAVGSL  TTAATGTGQG  PSTSTIPGPS  TEPSVVESKD
1081    RKANAHFILK  LLCDSVVLQP  YLRELLSAKD  ARGMTPFMSA  VSGRAYPAAI  TILETAQKIA
1141    KAEISSSEKE  EDVFMGMVCP  SGTNPDDSPL  YVLCCNDTCS  FTWTGAEHIN  QDIFECRTCG
1201    LLESLCCCTE  CARVCHKGHD  QKLKRTSPTA  YCDCWEKCKC  KTLIAGQKSA  RLDLLYRLLT
1261    ATNLVTLPNS  RGEHLLLFLV  QTVARQTVEH  CQYRPPRIRE  DRNRKTASPE  DSDMPDHDLE
1321    PPRFAQLALE  RVLQDWNALK  SMIMFGSQEN  KDPLSASSRI  GHLLPEEQVY  LNQQSGTIRL
1381    DCFTHCLIVK  CTADILLLDT  LLGTLVKELQ  NKYTPGRREE  AIAVTMRFLR  SVARVFVILS
1441    VEMASSKKKN  NFIPQPIGKC  KRVFQALLPY  AVEELCNVAE  SLIVPVRMGI  ARPTAPFTLA
1501    STSIDAMQGS  EELFSVEPLP  PRPSSDQSSS  SSQSQSSYII  RNPQQRRISQ  SQPVRGRDEE
1561    QDDIVSADVE  EVEVVEGVAG  EEDHHDEQEE  HGEENAEAEG  QHDEHDEDGS  DMELDLLAAA
1621    ETESDSESNH  SNQDNASGRR  SVVTAATAGS  EAGASSVPAF  FSEDDSQSND  SSDSDSSSSQ
1681    SDDIEQETFM  LDEPLERTTN  SSHANGAAQA  PRSMQWAVRN  TQHQRAASTA  PSSTSTPAAS
1741    SAGLIYIDPS  NLRRSGTIST  SAAAAAAALE  ASNASSYLTS  ASSLARAYSI  VIRQISDLMG
1801    LIPKYNHLVY  SQIPAAVKLT  YQDAVNLQNY  VEEKLIPTWN  WMVSIMDSTE  AQLRYGSALA
1861    SAGDPGHPNH  PLHASQNSAR  RERMTAREEA  SLRTLEGRRR  ATLLSARQGM  MSARGDFLNY
1921    ALSLMRSHND  EHSDVLPVLD  VCSLKHVAYV  FQALIYWIKA  MNQQTTLDTP  QLERKRTREL
1981    LELGIDNEDS  EHENDDDTNQ  SATLNDKDDD  SLPAETGQNH  PFFRRSDSMT  FLGCIPPNPF
2041    EVPLAEAIPL  ADQPHLLQPN  ARKEDLFGRP  SQGLYSSSAS  SGKCLMEVTV  DRNCLEVLPT
2101    KMSYAANLKN  VMNMQNRQKK  EGEEQPVLPE  ETESSKPGPS  AHDLAAQLKS  SLLAEIGLTE
2161    SEGPPLTSFR  PQCSFMGMVI  SHDMLLGRWR  LSLELFGRVF  MEDVGAEPGS  ILTELGGFEV
2221    KESKFRREME  KLRNQQSRDL  SLEVDRDRDL  LIQQTMRQLN  NHFGRRCATT  PMAVHRVKVT
2281    FKDEPGEGSG  VARSFYTAIA  QAFLSNEKLP  NLECIQNANK  GTHTSLMQRL  RNRGERDRER
2341    EREREMRRSS  GLRAGSRRDR  DRDFRRQLSI  DTRPFRPASE  GNPSDDPEPL  PAHRQALGER
2401    LYPRVQAMQP  AFASKITGML  LELSPAQLLL  LLASEDSLRA  RVDEAMELII  AHGRENGADS
2461    ILDLGLVDSS  EKVQQENRKR  HGSSRSVVDM  DLDDTDDGDD  NAPLFYQPGK  RGFYTPRPGK
2521    NTEARLNCFR  NIGRILGLCL  LQNELCPITL  NRHVIKVLLG  RKVNWHDFAF  FDPVMYESLR
2581    QLILASQSSD  ADAVFSAMDL  AFAIDLCKEE  GGGQVELIPN  GVNIPVTPQN  VYEYVRKYAE
2641    HRMLVVAEQP  LHAMRKGLLD  VLPKNSLEDL  TAEDFRLLVN  GCGEVNVQML  ISFTSFNDES
2701    GENAEKLLQF  KRWFWSIVEK  MSMTERQDLV  YFWTSSPSLP  ASEEGFQPMP  SITIRPPDDQ
2761    HLPTANTCIS  RLYVPLYSSK  QILKQKLLLA  IKTKNFGFV
```

FIGURE 5A
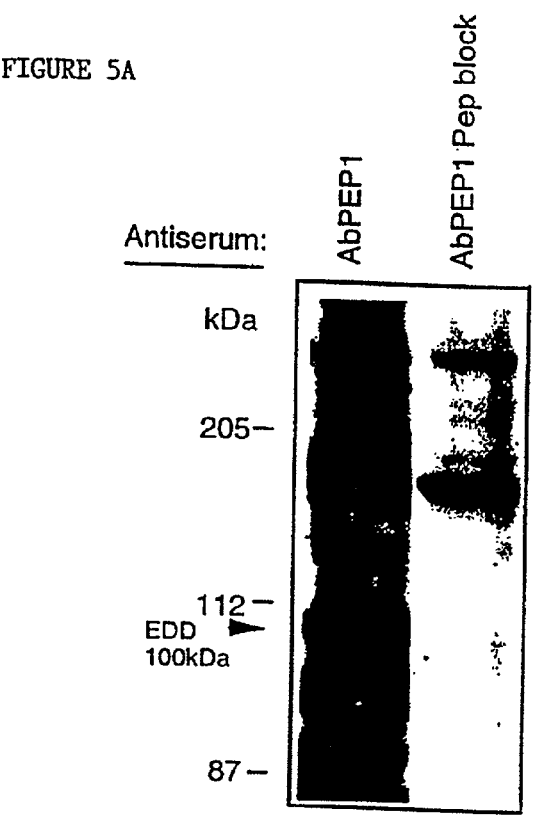
FIGURE 5 B
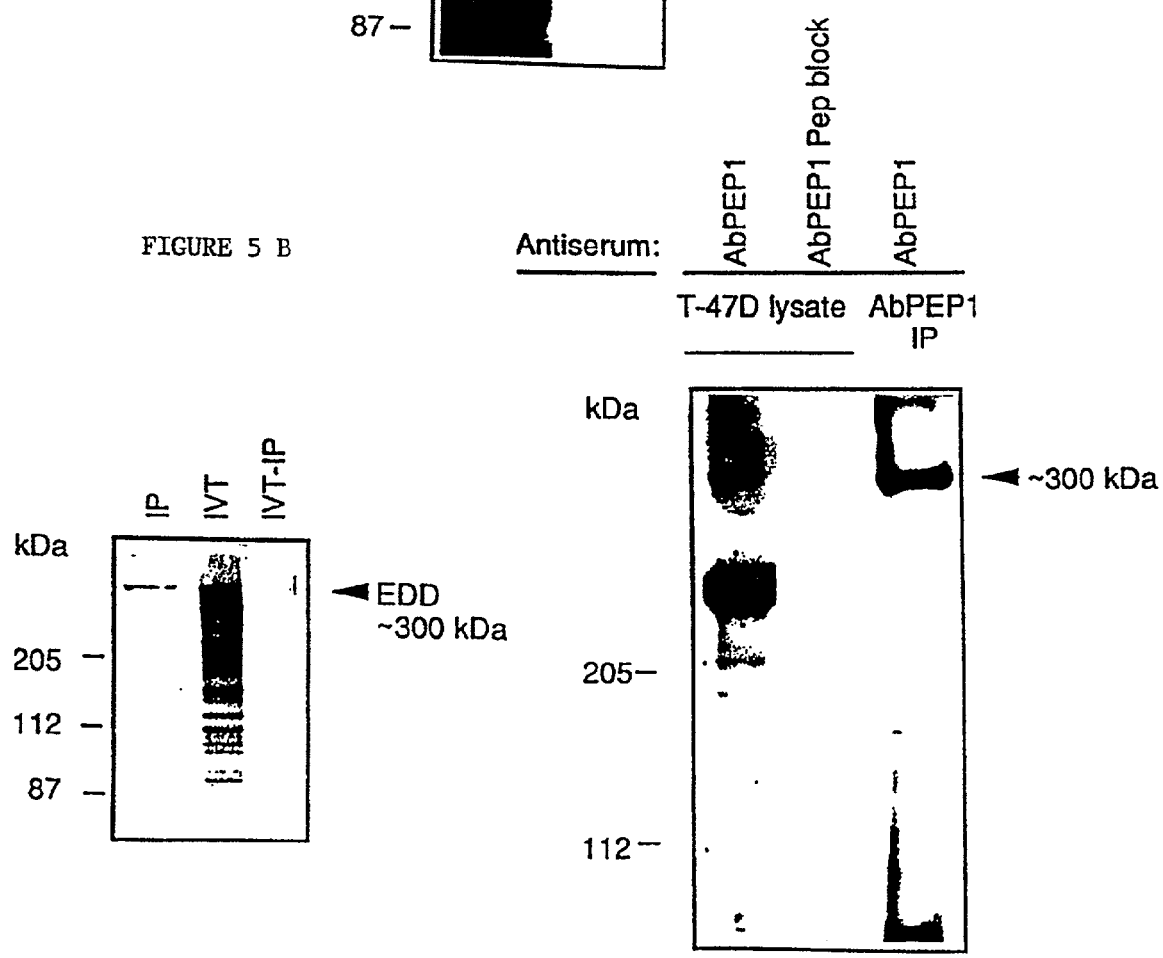
FIGURE 5C

HUMAN TUMOR SUPPRESSOR GENE

CROSS-REFERENCE TO RELATED APPLICATIONS

This application is a continuation of prior U.S. patent application Ser. No. 09/403,402, filed Oct. 21, 1999 now abandoned, which is 371 of International Application No. PCT/AU98/00280 filed Apr. 20, 1998, which claims foreign priority under 35 USC §119 from Australian Patent Application No. PO6334 filed Apr. 21, 1997.

FIELD OF THE INVENTION

This invention relates to a novel human progestin-regulated gene designated EDD (E3 isolated by Differential Display) which encodes a product exhibiting significant amino acid sequence identity with the HYD protein (hyperplastic discs) from *Drosophila melanogaster* and the 100 kDa HECT (homologous to E6-AP carboxyl terminus) domain protein from rat.

BACKGROUND OF THE INVENTION

The control of cell proliferation and differentiation in the normal breast and in breast cancer involves complex actions and interactions of steroid hormones (in particular estrogen and progesterone), peptide hormones and growth factors (1, 2). How these agents act at critical control points within the cell cycle to influence progression through the cycle or exit to enter a pathway of differentiation is only partially understood (3–5).

Progestins are responsible for mammary gland lobuloalveolar development during pregnancy (6), although there is evidence for a more predominant role for estrogens than progestins in stimulating epithelial cell proliferation in the normal premenopausal breast (7, 8). Progestins both stimulate and inhibit breast cancer epithelial cell proliferation in vitro but the predominant effect is growth inhibition probably via induction of differentiation (3, 4, 7, 9). Progestin action is mediated primarily through the progesterone receptor (PR), which acts as a transcriptional transactivator for a largely undefined set of progestin-responsive genes which may, in turn, transcriptionally or post-transcriptionally influence additional genes or gene products.

Only a limited number of genes have been implicated in progestin action on cell proliferation. Previous studies by the present inventors have identified c-myc and cyclin D1 as major downstream targets of progestin-stimulated cell cycle progression in human breast cancer cells (3, 10) while the delayed growth inhibitory effects of progestins involve decreases in cyclin D1 and E gene expression (4, 9). While progestin effects on c-myc gene expression are rapid and occur within minutes, effects on cyclin expression begin several hours later, pointing to the presence of undefined earlier events.

Since progestin action is complex and is likely to involve multiple genes, many of which are currently unknown, the differential display RT-PCR technique (DD-PCR) (11) was adopted to identify target genes in cultured human breast cancer cells. The utility of this approach has been previously demonstrated by the cloning of PRG1, a gene having significant homology with isoforms of 6-phosphofructo-2-kinase/fructose-2,6-bisphosphatase (12). Using the same technique, a novel progestin-regulated gene, EDD (designated DD5 in the applicant's Australian Provisional patent application No. PO6334), has been identified.

Based on amino acid sequence similarity, EDD appears to be a human homologue of the *Drosophila* tumor suppressor gene hyperplastic discs (hyd) (13). Although the function of the HYD protein is unknown, significant homology exists between its carboxyl terminus and those of human E6-AP and a number of proteins identified through database searches (14). These HECT domain family proteins function as ubiquitin-protein ligases (E3 enzymes) (14–16), playing a role in the ubiquitination cascade that targets specific substrate proteins for proteolysis. Notably, the protein encoded by EDD has a carboxy-terminal HECT domain containing a cysteine residue that covalently binds ubiquitin. This amino acid is conserved in all known HECT domain-containing E3 enzymes and is involved in the transfer of ubiquitin. It is therefore proposed that the EDD gene represents a novel human tumour suppressor gene encoding a ubiquitin-protein ligase.

DISCLOSURE OF THE INVENTION

In a first aspect, the present invention provides an isolated polynucleotide molecule comprising a nucleotide sequence encoding a protein, which comprises the following N-terminal amino acid sequence:

MTSIHFVVHP (SEQ ID NO:1)

or a biologically active fragment of said protein.

Preferably, the encoded protein comprises the following N-terminal amino acid sequence:

MTSIHFVVHPLPGTEDQLNDRLREVSEK-LNKYNLNSHPPLNVLEQATIKQ (SEQ ID NO:2).

More preferably, the encoded protein is ubiquitin-protein ligase and has an approximate molecular weight of 300 kDa.

Most preferably, the isolated polynucleotide molecule comprises a nucleotide sequence substantially corresponding to or, at least, ≧90% (more preferably, ≧95%) homologous to the nucleotide sequence shown at FIG. 3B from nucleotide 34 to nucleotide 8424 or a portion(s) thereof.

The term "fragment(s) thereof" in this regard is to be understood as referring to fragment(s) of the nucleotide sequence which encode biologically active peptide or polypeptide fragments or antigenic determinants. Typically, such "fragment(s) thereof" will comprise a nucleotide sequence of at least 50 nucleotides in length. However, shorter fragments of the nucleotide sequence (e.g. fragments of ≧8 nucleotides in length) may also be used in or for the production of probes useful for hybridization assays.

Thus, in a second aspect, the present invention provides an oligonucleotide or polynucleotide probe molecule labelled with a suitably detectable label (e.g. radioisotopes), comprising a nucleotide sequence substantially corresponding to, or complementary to, a ≧8 nucleotide portion of the nucleotide sequence shown at FIG. 3B from nucleotide 34 to nucleotide 8424.

Such probe molecules may be DNA or RNA. They may be used, for example, to quantitatively or qualitatively detect EDD mRNA in total or poly(A) RNA isolated from one or more tissues. As discussed below, such assays may have diagnostic and/or prognostic value.

The present invention also further extends to oligonucleotide primers for the above sequences, antisense sequences and homologues of said primers and antisense sequences, complementary ribozyme sequences, catalytic antibody binding sites and dominant negative mutants of the polynucleotide molecules.

Preferably, the polynucleotide molecule of the first aspect is of human origin. More preferably, the polynucleotide molecule is of human cancer cell origin.

The isolated polynucleotide molecule of the first aspect may be incorporated into plasmids or expression vectors or cassettes, which may then be introduced into suitable bacterial, yeast, insect or mammalian host cells. Such host cells may be used to express the protein or biologically active fragment thereof encoded by the isolated polynucleotide molecule.

As mentioned above, the amino acid sequence of the EDD product (pEDD) shows significant sequence similarity to the amino acid sequence of the HYD protein of Drosophila. The Drosophila hyd gene is a tumour suppressor gene and it is therefore expected that the EDD gene is similarly a tumour suppressor gene. Further, it is expected that the pEDD protein will have activity similar to the HYD protein. Particularly, inactivating or other mutations in EDD may give rise to susceptibility to cancer, thus making EDD a potential target for preventive or therapeutic strategies. Mutations in EDD could also be diagnostic for cancer susceptibility, particularly for early diagnosis in normal or pre-neoplastic disease or be useful in predicting tumour progression or response to therapy (i.e. a prognostic marker). Further, since EDD is likely to be involved in cell cycle regulation by progestins and other mitogens, EDD is a potential target for antiproliferative agents (i.e. cancer therapeutics). Moreover, as EDD is one of only a few known genes to be regulated by progestins, EDD is an important mediator of progestin action and a marker of clinical responsiveness to progestins.

As a tumour suppressor gene, EDD could be a familial cancer susceptibility gene, for example, like p16 (Multiple Tumor Suppressor Gene 1, MTS1) or the familial breast cancer susceptibility gene BRCA1. It might also have a role in sporadic cancer.

In a third aspect, the present invention provides in a substantially pure form, a protein (designated pEDD) comprising the following N-terminal amino acid sequence:

MTSIHFVVHP (SEQ ID NO: 1)

or a biologically active fragment of said protein.

Preferably, the protein of the third aspect comprises the following N-terminal amino acid sequence:

MTSIHFVVHPLPGTEDQLNDRLREVSEK-
LNKYNLNSHPPLNVLEQATIKQ (SEQ ID NO:2).

More preferably, the protein of the third aspect is a ubiquitin-protein ligase and has an approximate molecular weight of 300 kDa.

Most preferably, the protein of the third aspect comprises an amino acid sequence substantially corresponding to the amino acid sequence shown in FIG. 3C.

The biologically active fragments may consist of polypeptide or peptide sequences, which inhibit, mimic or enhance the biological effect of the protein. Additionally, the biologically active fragments may also represent antigenic determinants useful for raising antibodies specific to the protein.

The protein, or biologically active fragment thereof, according to the third aspect may be purified from natural sources (e.g. whole brain, heart, testis and appendix) or suitable cell lines, or may be produced recombinantly by any of the methods common in the art (Sambrook et at., 1989).

In a fourth aspect, the present invention provides a non-human organism transformed with the polynucleotide molecule of the first aspect of the present invention.

The organisms which may be usefully transformed with the polynucleotide molecule of the first aspect include bacteria such as E. coli and B. subtilis, eukaryotic cell lines such as CHO, fungi and plants.

In a fifth aspect, the present invention provides an antibody specific to the protein designated pEDD or an antigenic portion thereof The antibody may be polyclonal or monoclonal and may be produced by any of the methods common in the art.

It is also to be understood that the invention relates to kits for diagnostic assays, said kits comprising a protein or biologically active fragment thereof according to the second aspect and/or an antibody according to the fifth aspect. Additionally, or alternatively, the kit may comprise oligonucleotide probes for hybridisation assays or oligonucleotide primers for PCR based assays.

In a sixth aspect, the present invention provides a protein or antigenic portion thereof, capable of binding to an anti-pEDD antibody.

As will be seen hereinafter, in some tissues EDD appears to be regulated by progestin. EDD may, therefore, provide a useful marker for progestin-responsiveness in a subject. For example, as a marker of breast or endometrial tumour or meningioma responsiveness to progestins or progestin antagonists (antiprogestins)—i.e. high levels may indicate that the tumour is responsive to progestins/antiprogestins and could be sensitive to progestin/antiprogestin therapy. EDD may also be a useful prognostic marker since hormonally responsive tumours often have a better prognosis (i.e. patients have longer disease-free survival and overall survival). Alternatively, mutations, deletions or amplification of the EDD gene might predict tumour progression, and disease prognosis independent of its role a progestin-regulated gene. Thus, levels of EDD MRNA present in isolated cells or tissue samples may be assessed by DNA or RNA probes or primers in hybridisation assays or PCR analysis. Alternatively, the level of pEDD protein may be assessed through the use of the abovementioned antibodies.

Thus, in a seventh aspect, the present invention provides as assay for assessing progestin-responsiveness in a subject comprising the steps of;

(i) isolating cells or tissue from said subject; and (ii) detecting the presence of a protein comprising an amino acid sequence substantially corresponding to that shown at FIG. 3C .

In some circumstances, it may be preferred to expose the isolated cells or tissue to progestin or agonist or antagonist compounds and, subsequently, determine whether the progestin or agonist or antagonist compound has induced the production of the pEDD protein.

In an eighth aspect, the present invention provides a method for the diagnosis or determination of a predisposition to hyperproliferative disease, especially cancer, comprising detecting in a subject a polymorphism or alteration in the EDD gene which is indicative of said hyperproliferative disease or a predisposition to said hyperproliferative disease or developmental abnormality.

The modulation of EDD activity may also have therapeutic utility in the treatment of proliferative disorders, such as malignant or non-malignant hyperproliferative disease (e.g. breast and other cancers), and dermatological diseases or developmental abnormalities. Further, modulation of EDD may be of therapeutic value in processes involving progestin action in progestin target organs (e.g. fertility control, and reproductive tissue function).

EDD activity could be regulated by:

synthetic compounds, either stimulatory or inhibitory (i.e. agonists or antagonists), ribozymes specific for EDD (i.e. to down-regulate endogenous EDD activity), and gene therapy using expression vectors or oligonucleotides or other delivery systems (e.g. viral) containing a nucleotide sequence coding for EDD sense (i.e. to augment endogenous pEDD protein levels and activity) or antisense (i.e. to down-regulate endogenous pEDD protein levels and activity). Sense vectors could contain only a portion of the EDD coding sequence if separate desirable activities are found to reside in separate portions of the protein. Such vectors could also include dominant negative mutants of EDD which encode a gene product causing an altered phenotype by, for example, reducing or eliminating the activity of the endogenous pEDD protein. This might be caused through the interuption of formation of enzyme complexes, substrate competition or the formation of a defective substrate or reaction product. Particular examples of dominant negative mutants may be mutants that encode truncated proteins retaining pEDD sequences involved in protein-protein interactions or substrate recognition but which lack enzymatic or other activities residing elsewhere in the pEDD protein. Expression of such mutants would inhibit correct substrate modification or processing. Thus as a putative ubiquitin-protein ligase, truncated pEDD proteins could be expressed which allow the binding of. protein substrates but which lack the sequences necessary for the subsequent ubiquitination and destruction of these sequences.

Since the pEDD protein seems likely to be involved in cell cycle (growth) regulation including cell proliferation, differentiation and cell death, the pEDD protein or an agonist or antagonist might be used as a chemoprotectant in cancer chemotherapy treatments. That is, the pEDD protein or agonist/antagonist may be administered to a patient so as to stop the cell cycle including cell proliferation, differentiation and cell death in normal cells prior to treatment with standard cancer drugs (e.g. methotrexate, vinblastine and cisplatin). The arrested cells would thereby be less prone to damage by chemotherapy toxicity.

The term "substantially corresponding" as used herein in relation to the nucleotide sequence is intended to encompass minor variation(s) in the nucleotide sequence which due to degeneracy in the DNA code do not result in a change in the encoded protein. Further, this term is intended to encompass other minor variations in the sequence which may be required to enhance expression in a particular system but in which the variation(s) do not result in a decrease in biological activity of the encoded protein.

The term "substantially corresponding" as used herein in relation to amino acid sequence is intended to encompass minor variations in the amino acid sequence which do not result in a decrease in biological activity of the encoded protein. These variation(s) may include conservative amino acid substitutions). The substitution(s) envisaged are:

G,A,V,I,L,M; D, E; N,Q; S,T; K,R,H; F,Y,W,H; and P,Nα-alkalamino acids.

The terms "comprise", "comprises" and "comprising" as used throughout the specification, are intended to refer to the inclusion of a stated step, component or feature or group of steps, components or features with or without the inclusion of a further component or feature or group of steps, components or features.

The invention will hereinafter be further described by way of the following non-limiting example and accompanying figures.

BRIEF DESCRIPTION OF THE ACCOMPANYING FIGURES

FIG. 1. Identification of a differentially expressed cDNA in T-47D cells treated with the synthetic progestin ORG 2058.

A) Identification of EDD by differential display. Total RNA obtained from T-47D cells treated with ORG 2058 or vehicle control (ethanol) for 3 h was used as a template for differential display PCR reactions. The PCR products were separated on a 4.5% polyacrylamide denaturing gel and visualized by autoradiography. The arrow indicates the EDD DD-PCR product (DD5-1; see FIG. 3A) which is present at a higher level in the progestin treated (ORG 2058) compared with control lane.

B) Confirmation of the progestin induction of EDD by Northern blot analysis. T-47D cells proliferating in medium supplemented with 5% charcoal-treated FCS were treated with 10 nM ORG 2058 or ethanol vehicle (CONTROL) in the presence or absence of actinomycin D (ACT) and after 3 h total RNA was harvested for Northern analysis. The Northern blot was probed with the EDD clone P19.

C) Effect of cycloheximide on progestin induction of EDD mRNA. T-47D cells proliferating in medium supplemented with 5% charcoal-treated FCS were treated with ORG 2058 (10 nM), cycloheximide (CHX, 20 μg/ml), ORG 2058 and CHX simultaneously or ethanol vehicle and harvested for total RNA at 1 h. The Northern blot was probed with the EDD DD-PCR fragment DD5-1.

FIG. 2. Expression of EDD mRNA in human tissues.

A) Northern blot analysis of polyA$^+$ RNA from human tissues. The blot was hybridized with the P19 cDNA clone of EDD. Molecular sizes of markers are indicated. PBL, peripheral blood leukocytes.

B) Dot blot analysis of polyA$^+$ RNA from human tissues. The blot was hybridized with the P19 cDNA clone of EDD. Row A: 1, whole brain; 2, amygdala; 3, caudate nucleus; 4, cerebellum; 5, cerebral cortex; 6, frontal lobe; 7, hippocampus; 8, medulla oblongata; Row B: 1, occipital lobe; 2, putamen; 3, substantia nigra; 4, temporal lobe; 5, thalamus; 6, sub-thalamic nucleus; 7, spinal cord; Row C: 1, heart; 2, aorta; 3, skeletal muscle; 4, colon, 5, bladder; 6, uterus; 7, prostate; 8, stomach; Row D: 1, testis; 2, ovary; 3, pancreas; 4, pituitary gland; 5, adrenal gland; 6, thyroid gland; 7, salivary gland; 8, mammary gland; Row E: 1, kidney; 2, liver; 3, small intestine; 4, spleen; 5, thymus; 6, peripheral leukocyte; 7, lymph node; 8, bone marrow; Row F: 1, appendix; 2, lung; 3, trachea; 4, placenta; Row G: 1, fetal brain; 2, fetal heart; 3, fetal kidney; 4, fetal liver; 5, fetal spleen; 6, fetal thymus; 7, fetal lung.

FIG. 3. Cloning and predicted amino acid sequence of EDD.

A) A schematic representation of EDD structure with a restriction map for the EDD cDNA indicating the sites used for cloning the full-length EDD construct and the cDNA clones used to derive the EDD sequence shown beneath. The DD-PCR cDNA fragment identified by differential display was designated DD5-1 and a cDNA clone derived from the 5' RACE product and the original DD-PCR product, DD5-2. All cDNA clones were isolated from a human placenta cDNA library with the exception of H1 which was isolated from a human heart cDNA library.

B) The nucleotide sequence of EDD (SEQ ID NO:5). The start and stop codons are underlined.

C) Predicted amino acid sequence of pEDD (SEQ ID NO:4). There are two regions with high homology (~60%) to HYD (a central sequence and a carboxyl sequence containing the HECT domain) and these and other highly conserved sequences are shown in bold type, while two putative nuclear localization signals are boxed. The HECT domain is underlined and in bold type and includes a conserved cysteine at residue 2768 (boxed). A region showing homology to polyA-binding proteins is italicized and the peptide sequence to which antiserum AbPEP1 was raised is underlined. The numbers refer to positions of amino acids.

Figure 4:

FIG. 4. Chromosomal localization of the EDD gene.

Metaphase showing FISH with the H1 probe. Normal male chromosomes were stained with DAPI. Hybridization sites on chromosome 8 are indicated by an arrow.

FIG. 5. Characterization of EDD protein.

A) Detection of recombinant EDD protein with AbPEP1. Sf9 cells infected with baculovirus containing a truncated EDD construct (EDD 100 kDa) were boiled in SDS-sample buffer prior to SDS-PAGE through a 6% gel, transferred to nitrocellulose and blotted with AbPEP1 or AbPEP1 peptide-blocked.

B) Determination of the size of the EDD protein. EDD was immunoprecipitated from T-47D lysate using AbPEP1. The immunoprecipitate (IP) was resolved by SDS-PAGE through a 6% gel alongside the products of in vitro translated full length EDD (IVT) and immunoprecipitated in vitro translated EDD (IVT-IP). The T-47D immunoprecipitate was transferred to nitrocellulose and blotted for EDD with AbPEP1 while the remainder of the gel was dried and autoradiographed. Molecular masses of marker proteins are indicated.

C) Detection of EDD protein in T-47D lysates. Immunoprecipitated EDD was run alongside 40 μg total protein from T-47D lysate. Total proteins were blotted with either AbPEP1 or peptide-blocked AbPEP1 and the immunoprecipitate was blotted with AbPEP1.

Figure 6:
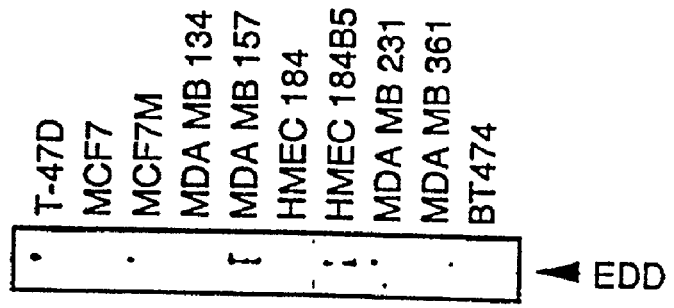

FIG. 6. EDD protein expression in human tissues and cell lines.

Expression of EDD in normal breast and breast cancer cell lines. Total cell lysates from a range of cell lines were separated by SDS-PAGE through a 6% gel, transferred to nitrocellulose and blotted with AbPEP1. 184 is a normal breast cell line, 184B5 an immortalized derivative, and the remainder are breast cancer cell lines, MCF-7M being a sub-line of MCF-7.

Figure 7:
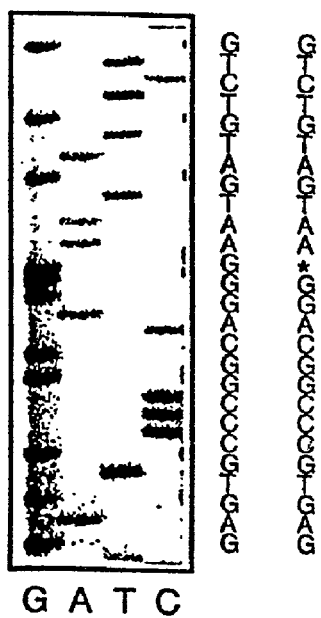

FIG. 7. Sequence of the rat 100 kDa protein cDNA.

Autoradiograph of the sequencing gel obtained when one clone was sequenced using the EDD-specific FC2 primer, with the sequence (a) listed alongside the autoradiograph. The published sequence (b,) is shown alongside and the missing base denoted by an asterisk.

FIG. 8. Ubiquitin thiol ester formation by EDD.

In vitro translation of truncated (A) or full-length (B) EDD wild type or mutant (C2768A) protein in the presence of $^{35}$S-methionine was followed by a 10 min incubation at 25° C. either with or without purified GST-ubiquitin (or GST in part A) fusion protein. Samples were resolved by SDS-PAGE (A, 7% gel; B, 6% gel) following either incubation at 25° C. for 20 min in non-reducing sample buffer containing 4 M urea or boiling in sample buffer containing 100 mM DTT. Ubiquitin- and GST-ubiquitin-bound forms are marked with arrows.

EXAMPLE

Materials and Methods

Reagents

Steroids and growth factors were obtained from the following sources: ORG 2058 (16a-ethyl-21-hydroxy-19-norpregn-4-en-3,20-dione), Amersham Australia Pty Ltd, Sydney, Australia; human transferrin, Sigma Chemical Co., St. Louis, Mo.; and human insulin, Actrapid, CSL-Novo, North Rocks, Australia. Steroids were stored at −20° C. as 1000-fold-concentrated stock solutions in absolute ethanol. Cycloheximide (Calbiochem-Behring Corp., La Jolla, Calif.) was dissolved at 20 mg/ml in water and filter sterilized. Actinomycin D (Cosmegen, Merck Sharp and Dohme Research Pharmaceuticals, Rahway, N.J.) was dissolved at 0.5 mg/ml in sterile water and used immediately. Tissue culture reagents were purchased from standard sources.

Cell Culture

The sources and maintenance of the human breast cancer and normal cell lines used were as described previously (12, 22), as were tissue culture experiments (12). Briefly, progestin (ORG 2058, 10 nM) and/or cycloheximide (20 μg/ml) or actinomycin D (5 μg/ml) was added to the medium and control flasks received the same volume of vehicle alone. To obtain RNA for differential display, cells were grown in insulin-supplemented serum-free medium and treated for 3 h with ORG 2058 or ethanol vehicle. Subsequent progestin stimulation experiments were carried out in medium containing 5% charcoal-stripped fetal calf serum without insulin.

RNA Isolation and Northern Analysis

Cells harvested from duplicate 150 cm$^2$ flasks were pooled, RNA extracted by a guanidinium-isothiocyanate-cesium chloride procedure and Northern analysis was performed as previously described with 20 μg of total RNA per lane (3, 23). The membranes were hybridized overnight (50° C.) with probes labelled with [a-$^{32}$P]dCTP (Amersham Australia Pty Ltd) using a Prime-a-Gene labelling kit (Promega Corp., Sydney, Australia). The membranes were washed at a highest stringency of 0.2 ¥ SSC (30 mM NaCl, 3 minN sodium citrate [pH 7.0])/1% sodium dodecyl sulfate at 65° C. and exposed to Kodak X-OMAT or BIOMAX film at −70° C. Human multiple tissue Northern blots or RNA Master blot (CLONTECH Laboratories Inc., Palo Alto, Calif.) were hybridized under conditions recommended by the manufacturer. The MRNA abundance was quantitated by densitometric analysis of autoradiographs using Molecular Dynamics Densitometer and software (Molecular Dynamics, Sunnyvale, Calif.). The accuracy of loading was estimated by re-hybridizing membranes with a [g-$^{32}$P]ATP end-labelled oligonucleotide complementary to 18S rRNA (24, 25).

Differential Display

Differential display was carried out as previously described (11) using a Heiroglyph mRNA Profile Kit No. 1 (Genomyx Corporation, Foster City, Calif.) and recommended protocol. First strand cDNA synthesis was carried out in 96-well format 0.2 ml thin walled tubes. Typically 200 ng total RNA from T-47D cells treated with the synthetic progestin ORG 2058 for 3 h or from control T-47D cells was reverse transcribed with Expand Reverse Transcriptase enzyme (Boehringer Mannheim Pty Ltd, Castle Hill, Australia) following annealing with 4 pmol anchored primer (5'ACGACTCACTATAGGGCT$_{12}$AC (SEQ ID NO:6)). Subsequent PCR amplification was performed with one-tenth of the resultant cDNA in duplicate reactions containing [α-$^{33}$P] dATP with the anchored primer (0.2 μM), an arbitrary primer (5'ACAATTTCACACAGGAGCTAGCAGAC (SEQ ID NO:7), 0.2 μM) and Expand Long Template Taq DNA Polymerase (Boehringer Mannheim). The PCR products were denatured and separated on a 4.5% denaturing polyacrylamide gel at 800 v for 16 h using the Genomyx Long Read Sequencing System reagents and apparatus. The gel was dried on the glass plate and exposed to X-ray film for 16–72 h. The DD-PCR product of interest was excised from the gel and amplified by PCR under the conditions recommended by the kit manufacturer using an M13 forward primer (5'AGCGGATAACAATTTCACACAGGA) (SEQ ID NO:8) and a T7 promoter primer (5'TAATAC-GACTCACTATAGGG (SEQ ID NO:9)). The reamplified PCR products were purified from 0.8% agarose gels using QIAEX reagents (Qiagen Pty Ltd, Clifton Hill, Australia).

Cloning and Sequencing of cDNAs

Double stranded DNA templates were sequenced using the fmol DNA Cycle Sequencing System (Promega Corp.) with [$^{33}$P]-labelled primers. The M13 primer was used for direct sequencing of DD-PCR products and the T7 and SP6 (5'GATTTAGGTGACACTATAG (SEQ ID NO:10)) promoter primers were used for sequencing PCR products cloned into the pGEM-T vector (Promega Corp.). Sequence database searches were performed at the NCBI using the Blast or Fasta network services. Peptide motif searches were carried out against the Prosite database.

Two primers (FC2: 5'GACGAAGGGCCCTGACT-GCGCGAGAAGAAGC (SEQ ID NO:11) and R2: 5'AAA-GAATTCTGTCATGGAGTCTGAACGTCG (SEQ ID NO:12)) that flank the region containing the reported rat 100 kDa start codon (26) were used to amplify cDNA extracted from a rat hypothalamus library (CLONTECH). The resulting PCR product was cloned into pGEM-T (Promega Corp.) and four clones were sequenced.

Rapid Amplification of cDNA 5' ends (5'RACE)

Additional sequence was obtained with the aid of a 5'RACE kit (Life Technologies Inc., Gaithersburg, Md.), following the manufacturer's instructions. Briefly, a gene specific primer (GSP 1: 5'CACGCTCCAATGCAAGCTGG (SEQ ID NO:13)) was used to prime first strand cDNA synthesis. Following removal of the RNA strand, cDNA was 5' poly dC tailed and amplified by PCR. The target cDNA was amplified using an anchor primer (UAP: 5'GGC-CACGCGTCGACTAGTACGGGIIGGGIIGGGIIG (SEQ ID NO:14), where I represents deoxyinosine) in combination with a second gene specific primer (GSP2: 5'CGATCT-TCCCTGATTCGAGGTGGC (SEQ ID NO:15)). Various gel-purified PCR products were further PCR amplified, primed by UAP and a third gene specific nested primer (GSP3: 5'CTGTATTGACAATGCTCCACC (SEQ ID NO:16)).

cDNA Library Screening $10^6$ plaques from a human heart cDNA library in the Lambda ZAPII vector primed with both oligo (dT) and random primers (Stratagene, La Jolla, Calif.) were transferred to nylon membranes (Hybond N, Amersham Australia Pty Ltd) and screened with both the original DD-PCR fragment and the RACE product as [$^{32}$P]-labelled probes. This led to isolation of clone H1 (2.55 kb). This clone and the RACE product were used to screen $10^6$ recombinants from a human placenta 5'-STRETCH PLUS cDNA library in lgt10 primed with both oligo (dT) and random primers (CLONTECH Laboratories, Inc.). Sequencing of cDNA clones in either bluescript or lgt10 was carried out as described above using vector-specific or gene-specific primers. Several rounds of isolation of positive clones and further screening of this library led to the isolation of the following overlapping clones covering the entire EDD open reading frame: P61 (1.95 kb), P43 (2.1 kb), P1 (1.5 kb), P19 (3 kb) and P47 (2.1 kb).

Fluorescence in situ Hybridization

A probe corresponding to clone H1 was nick-translated with biotin-14-dATP and hybridized in situ at a final concentration of 20 ng/ml to metaphases from two normal males. The fluorescence in situ hybridization (FISH) method was modified from that previously described (27) in that chromosomes were stained before analysis with both propidium iodide (as counterstain) and DAPI (for chromosome identification). Images of metaphase preparations were captured by a CCD camera using the CytoVision Ultra image collection and enhancement system (Applied Imaging Int Ltd). FISH signals and the DAPI banding pattern were merged for figure preparation.

Figure 3A:
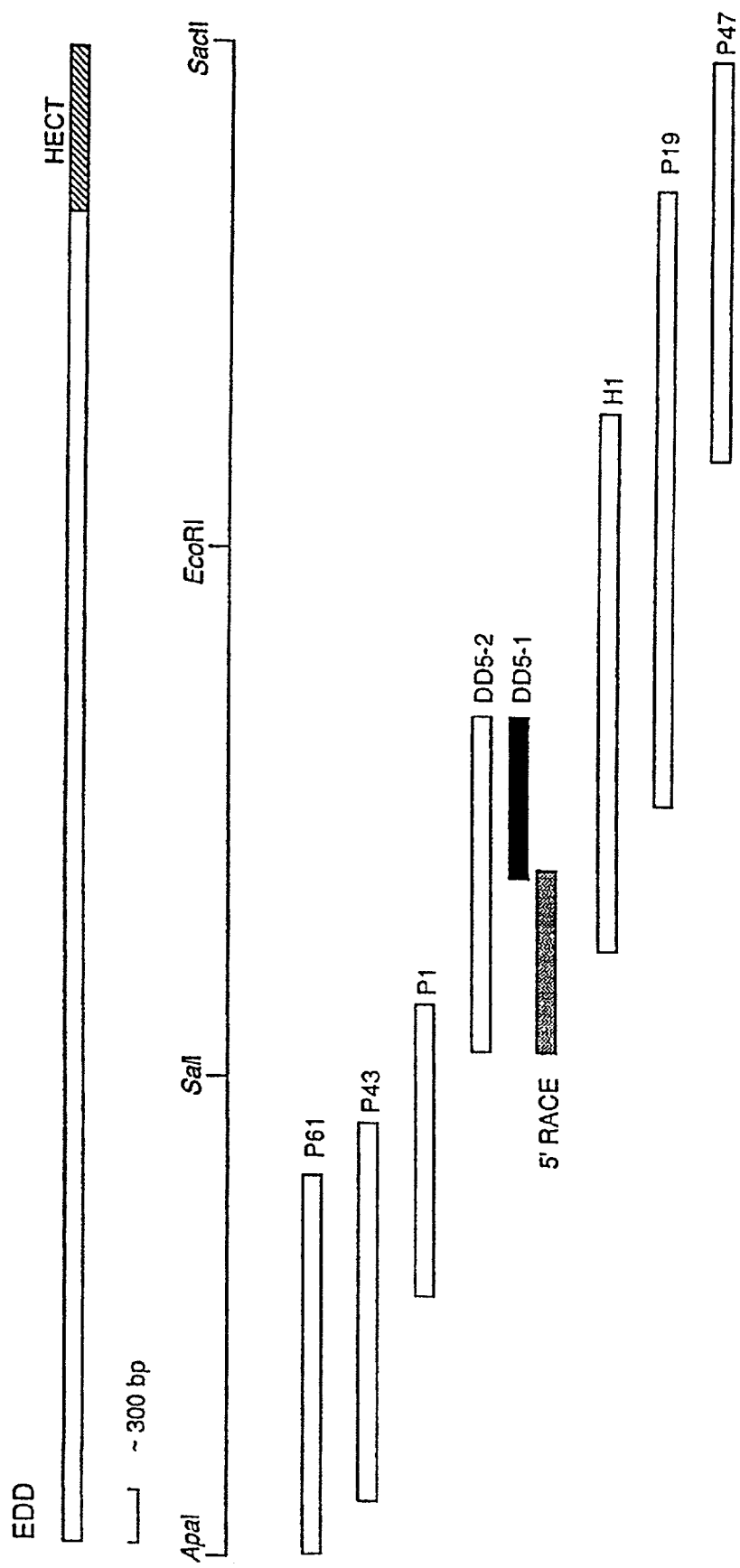

Construction of Recombinant cDNA Clones for in vitro Translation and Protein Expression The full length EDD sequence was cloned by ligating three PCR products. which spanned the open reading frame into bluescript. The existing SalI and EcoRI restriction sites used to ligate the fragments are indicated in FIG. 3A. The carboxyl third of the cDNA was cloned into bluescript such that an 890 amino acid truncated protein corresponding to the predicted rat 100 kDa protein (from aa 1910 to aa 2799) would be translated. An identical truncated cDNA fragment was cloned into the PFASTBAC 1 expression vector (Life Technologies Inc.) for protein expression using the BAc-TO-BAc baculovirus expression system in Spodoptera frugiperda (Sf9) cells and full length EDD cDNA was cloned into the pRcCMV expression vector (Invitrogen, Leek; The Netherlands) for transient transfection into HEK-293 cells. Mutagenesis of cysteine 2768 to alanine was performed for full length and truncated constructs in pBluescript using the Quick-Change site-directed mutagenesis kit (Stratagene). In vitro transcription and translation were performed using the TNT T7 Quick coupled rabbit reticulocyte lysate system (Promega Corp.) and [$^{35}$S]-methionine (1000 Ci/mmole, ICN Biomedicals Australasia Pty Ltd, Seven Hills, Australia).

SDS-polyacrylamide Gel Electrophoresis (PAGE) and Immunoblotting

Cells growing in mid-log phase were lysed in 1% Triton X100 buffer containing 50 mM 4-(2-Hydroxyethyl) -1-piperazineethanesulfonic acid (HEPES; pH 7.5), 150 mM NaCl, 10% glycerol, 1.5 mM $MgCl_2$, 1 mM EGTA, 10 mM sodium pyrophosphate, 20 mM sodium fluoride, 1 mM dithiothreitol (DTT), 10 µg/ml each of aprotonin and leupeptin, 1 mM phenylmethylsulfonyl fluoride (PMSF) and 200 µM sodium orthovanadate. Lysates were cleared by centrifugation, quantitated according to a modified Bradford method (Bio-Rad Laboratories, Hercules, Calif.) and typically 40 µg of total protein in SDS-sample buffer (50 mM Tris-HCl, pH 6.8, 2% SDS, 10% glycerol, and 0.2% bromophenol blue) containing 5% b-mercaptoethanol were resolved on 6% SDS-polyacrylamide gels. Following electrophoresis proteins were transferred to nitrocellulose (TransBlot, Bio-Rad Laboratories) and subjected to immunodetection. An EDD-specific peptide (SSEKVQQEN-RKRHGSS (SEQ ID NO:17)) was synthesised, coupled via glutaraldehyde to diptheria toxoid and used to generate a rabbit anti-EDD antibody (designated AbPEP1).

Immunoprecipitation

Cleared cell lysates (typically 1 mg total protein) orin vitro translation reactions were incubated with either control rabbit serum or AbPEP1 in the presence or absence of a 10-fold excess of competing peptide for 1-2 hr at 4° C. Following incubation with Protein A Sepharose 4B (Zymed, San Francisco, Calif.), immunoprecipitates were washed three times in 1% Triton X100 lysis buffer described above, resolved by SDS-PAGE and either transferred to nitrocellulose and immunoblotted with AbPEP1 or where applicable dried onto Whatman 3 MM paper and subjected to autoradiography.

Ubiquitin-binding Assay

[$^{35}$S]-labelled in vitro translated truncated (~100 kDa) or full length protein was tested for its ability to bind ubiquitin by incubating 5 µl translation reaction with or without 5 µg purified GST protein or GST-ubiquitin fusion protein for 10 min at 25° C. (28). Reactions were terminated by incubating the mixtures in either SDS-sample buffer containing 100 mM DTT at 95° C. for 5 min or in SDS-sample buffer containing 4 M urea instead of DTT at 25° C. for 20 min. Samples were resolved by SDS-PAGE through 6% or 7% gels followed by drying and autoradiography.

Results

Isolation and Northern Blot Analysis of a Progestin Regulated cDNA

Figure 1B:
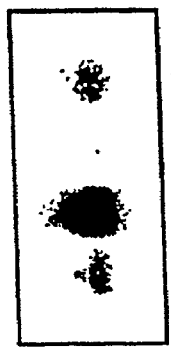
Figure 1C:
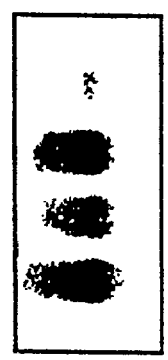

The differential display technique was used to identify mRNAs in T-47D human breast cancer cells with altered levels of expression in response to treatment with the synthetic progestin ORG 2058 for 3 h. When the anchored primer, 5'ACGACTCACTATAGGGCTI$_{12}$AC (SEQ ID NO:6) was used in conjunction with the arbitrary primer, 5'ACAATTTCACACAGGAGCTAGCAGAC (SEQ ID NO:7), a cDNA fragment of approximately 850 bp that was more abundant in treated samples than in control samples was identified and designated EDD (FIG. 1A). Northern analysis of total cellular RNA from T-47D cells showed that transcription was required for the observed ORG 2058 induction of EDD mRNA levels as this was blocked in the presence of actinomycin D (FIG. 1B). Induction was also prevented by cycloheximide, suggesting that EDD is not directly transcriptionally regulated by progestin acting via the PR (FIG. 1C).

The tissue specificity of EDD gene expression was investigated by hybridizing Northern blots of polyA$^+$ RNA isolated from human tissues to the EDD cDNA fragment. A single transcript of 9.5 kb was detected in a variety of tissues (FIG. 2A) with the highest expression in testis, heart, placenta and skeletal muscle. Hybridization to a more quantitatively loaded RNA dot blot (FIG. 2B) confirmed that EDD is expressed at varying levels in all tissues examined and that the MRNA was most abundant in testis and expressed at high levels in brain, pituitary and kidney. Significant levels of expression were also observed in placenta, uterus, prostate, stomach, fetal lung and various brain tissues. EDD MRNA was also expressed in a range of breast cancer cell lines, not all of which are progestin-responsive (not shown).

Cloning of the Full Length EDD cDNA

The original DD5-1 fragment isolated by DD PCR was 850 bp in length and is shown schematically in FIG. 3A. The DNA sequence of this fragment had no homology to sequences of any known human genes. To obtain the complete coding sequence from which MDD was derived a combination of 5'RACE and screening of human heart and placenta cDNA libraries was used. This resulted in a series of overlapping clones covering 8.5 kb of sequence (FIG. 3A; Genbank Accession AF006010). Analysis of the nucleotide sequence (FIG. 3B) revealed an open reading frame of 2799 amino acids (FIG. 3C). The EDD sequence was divided into overlapping 1800 bp segments and used in Blastx searches of the GenBank database. The only homology to a human sequence of known function was to polyA binding protein across 50 amino acids (50%, FIG. 3C) although the similarities among mammalian polyA binding proteins in this stretch are usually in the vicinity of 100%.

The DNA sequence of EDD showed significant similarity to two sequences in the database. Both of these genes encode proteins belonging to the HECT family of ubiquitin-protein ligases, although their specificities are unknown. HECT proteins contain a conserved domain of approximately 300 amino acids that contains a cysteine residue able to bind ubiquitin via a thioester linkage. Nucleotides 5667 to 8502 of EDD were 88% identical to the rat 100 kDa protein cDNA sequence (26), nucleotides 572 to 740 and 3498 to 3867 were 69% identical to two regions of the *Drosophila melanogaster* hyperplastic discs gene (hyd) and nucleotides 7560 to 8430 were 60% identical to a third region of hyd (13). The putative initiation codon is surrounded by a consensus sequence for strong translational initiation (ACCATGA, (29)) and corresponds to a possible start codon of the *Drosophila* hyd gene (13). The stop codon corresponds to that shared by the rat 100 kDa protein and hyd genes. Like EDD, both the hyd and rat 100 kDa protein genes have estimated mRNA transcript sizes of 9.5 kb (14, 26). The predicted EDD protein is identical to HYD at 40% of amino acid residues and similar at 64% of residues, while the carboxyl third of EDD is 96% identical and 98.5% similar to rat 100 kDa protein. The most highly conserved regions between HYD and EDD are designated by bold type in FIG. 3C. Within two of these regions there are stretches of 40–80 amino acids that are highly conserved between HYD, EDD and a possible *C. elegans* homologue of HYD contained within 2 overlapping cosmids (Genbank Accession No. G1729554 and G1729549). The longest conserved regions between EDD and HYD are a central domain of approximately 400 amino acids (58% identity, 72% similarity) and the carboxyl 300 amino acids which include the HECT domain and conserved cysteine residue (64% identity, 80% similarity). This latter region also showed around 30% identity and 50% similarity with other HECT proteins including yeast RSP5 or PUB-1 and RAD26 (14, 30, 31), and the mammalian proteins UreB1 (19), Nedd-4 (15, 20, 32, 33) and E6-AP (15, 17, 18). Apart from two putative nuclear localization signals (34), no other consensus functional domains were identified within the EDD sequence.

Chromosomal Localization of the EDD Gene

FISH was used to localize the gene for EDD. Eighteen metaphases from a normal male were examined for fluorescent signal. Seventeen of these metaphases showed signal on one or both chromatids of chromosome 8 in the region q22. High resolution studies of 8 metaphases showed signal at q22.3 (FIG. 4). There was a total of 4 non-specific background dots observed in these 18 metaphases. A similar result was obtained from hybridization of the probe to 11 metaphases from a second normal male (data not shown). This localization was consistent with independent assignment of an EST corresponding to EDD (EST116344) using the radiation hybrid panel Genebridge 4.

Characterization of EDD Protein

A rabbit antiserum (AbPEP1) against an EDD-specific peptide matching a sequence towards the carboxyl terminus of the protein (underlined in FIG. 3C) reacted strongly on Western blots with a truncated (100 kDa) recombinant EDD protein expressed in Sf9) cells using a baculovirus system (FIG. 5A). A second strongly reactive band of approximately 200 kDa was also seen, but this appeared to be non-specific as antibody binding was not competed by the EDD peptide. The full length EDD cDNA was cloned into bluescript and translated in vitro in a rabbit reticulocyte lysate system. The size of the major product was in agreement with the expected molecular mass of the protein as predicted from the amino acid sequence (~300 kDa, FIG. 5B). The identity of the translated protein was confirmed by immunoprecipitation from either translation reactions or T-47D whole cell lysates with AbPEP1 (FIG. 5B). Western blotting of whole cell lysates from T-47D cells using AbPEP1 detected two major bands, both abolished in the presence of competing peptide—a major species at approximately 230 kDa and a minor species of higher molecular mass (FIG. 5C). This latter band corresponds in size to that of the in vitro translated protein and is immunoprecipitated by AbPEP1 (FIG. 5C) and by two other EDD-specific peptide antibodies (not shown). However, the 230 kDa protein is not immunoprecipitated from cell lysates by these antibodies. As a single EDD mRNA transcript was detected on Northern blots, it was hypothesised that the EDD protein may be processed to the 230 kDa form which could be folded in such a way that was not susceptible to immunoprecipitation in its native state. However, transient expression of full length EDD in HEK-293 cells followed by Western blotting of whole cell lysates revealed an increase in the expression of the 300 kDa species only (not shown). Western blotting of whole cell lysates from a number of normal breast and breast cancer epithelial cell lines showed that EDD protein was expressed in all immortalized and cancer cell lines but not in a normal breast cell line, 184 (FIG. 6).

Identity of the Rat Gene Product

The previously described rat cDNA that is highly homologous to the EDD gene reportedly gives rise to a 100 kDa protein, inferred from cDNA sequence data which showed several in-frame stop codons upstream of the putative initiation codon (26), corresponding to amino acid residue 1910 of EDD. These stop codons were not present in the EDD cDNA. Furthermore, although we were able to confirm that an anti-HYD antibody detected an approximately 100 kDa protein in rat muscle lysates, this species was not detected by AbPEP1 even though the predicted sequences of human and rat proteins are identical at every residue of the peptide used to raise the AbPEP1 antibody. This led the present inventors to question whether the 100 kDa protein was the actual rat gene product.

A segment of rat cDNA was cloned containing the stretch of sequence upstream of the proposed initiation codon and found an additional base that, by changing the reading frame, removes the upstream stop codons (FIG. 7). Correction of this apparent error results in a rat cDNA sequence that closely matches the human cDNA, in which a continuous open reading frame exists throughout the sequence. While the rat cDNA sequence corresponding to the amino terminal two-thirds of EDD has not been cloned, a number of mouse expressed sequences covering parts of this region are recorded in the GenBank database (Accession No. AA183561, AA177260, AA183970, AA231351, AA087561) and these show similar levels of similarity with the EDD DNA sequence as that seen with the published rat sequence. Thus it appears that the true product of the rat gene is not a 100 kDa protein but may exist as a larger species. In rat lysates, however, AbPEP1 does not detect a protein having a molecular weight consistent with the human (EDD) and Drosophila (HYD) gene products.

Ubiquitin Binding by EDD

A critical feature of the HECT family of E3 enzymes is their ability to reversibly form thioesters with ubiquitin at a conserved cysteine residue within the HECT domain. This property has been demonstrated for the HECT proteins human E6-AP, rat 100 kDa protein and yeast RSP5 where the thioester linkage remains intact in the absence of reducing agents but is broken in the presence of 100 mM DTT (14). Substitution of the conserved cysteine residue prevents ubiquitin thioester bond formation. However, this property has not been shown for the HYD protein. To assess the potential of EDD to function as an E3 we tested whether EDD could form a reversible bond with ubiquitin via the conserved cysteine, C2768. $^{35}$S-labelled in vitro translated truncated protein (~100 kDa of carboxyl terminus sequence) was incubated with purified GST-ubiquitin fusion protein in the presence or absence of DTT before SDS-PAGE (FIG. 8A).

Figure 8A:
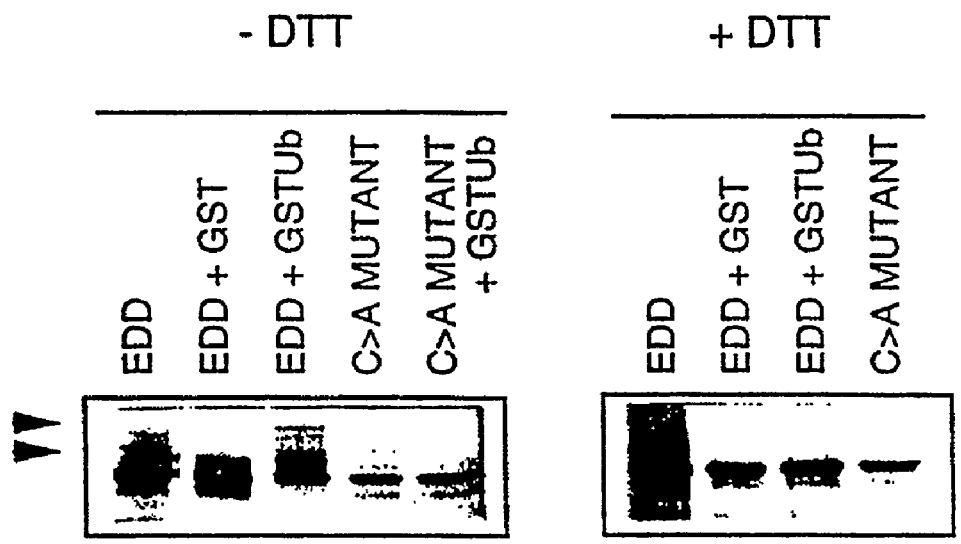
Figure 8B:

In the absence of DTT an additional higher molecular mass protein band was observed that corresponded to the expected size of an EDD-GST-ubiquitin conjugate (~130 kDa, upper arrow in FIG. 8A). This species was abolished in the presence of 100 mM DTT suggesting involvement of a thioester bond in its formation. This was confirmed by experiments with an in vitro translated protein containing a C2768A mutation: binding of GST-ubiquitin was not seen under these conditions (FIG. 8A). A species of slightly higher molecular mass than EDD was also observed (lower arrow in FIG. 8A), consistent with the formation of ubiquitin-EDD conjugates, ubiquitin being present as a component of the rabbit reticulocyte lysate. Again this was not observed using the mutant protein or in the presence of 100 mM DTT. Similar results were achieved with full length EDD protein obtained (though at lower yield) by in vitro translation (FIG. 8B).

Discussion

Application of the differential display PCR technique to a cultured human breast cancer cell model in which clearly defined proliferative responses to progestins are observed has led to the identification of a novel gene, EDD, a likely human homologue of the Drosophila melanogaster tumor suppressor gene hyperplastic discs (13). EDD is also highly homologous to the partial published sequence for the cDNA encoding the rat 100 kDa protein (26). All three genes produce large (approx 9.5 kb) mRNAs and the predicted entire EDD open reading frame of 2799 amino acids shares 40% identity with that of Drosophila hyd while the carboxyl-terminal 889 amino acids of EDD share 96% identity with the rat protein. Western analysis showed that the EDD gene product is a protein of approximately 300 kDa. This protein is also immunoprecipitated by 3 different peptide-specific EDD antibodies and also corresponds to the size of the major in vitro translated gene product. The large discrepancy in the predicted size of the human and rat proteins was apparently resolved by re-examination of the rat cDNA sequence which disclosed an error in the published translation start site, pointing to the likelihood that a larger gene product exists.

At their carboxyl termini EDD, its rat homologue and HYD all contain a highly homologous HECT domain, indicating membership of a larger family of proteins which function as ubiquitin protein ligases (E3s). The ubiquitination of target proteins occurs by the action of multiple interacting proteins: a ubiquitin-activating enzyme (E1), ubiquitin-conjugating enzymes (E2) and ubiquitin-protein ligases (E3). Substrate specificity is largely determined by E3s, which bind and transfer ubiquitin to the target protein following interaction with specific E2s. The key feature of the HECT class of E3s is their ability to covalently bind ubiquitin through a conserved cysteine residue located in their HECT domains (14). This property was demonstrated for EDD using in vitro translated protein that lost the ability to bind ubiquitin if the conserved cysteine (C2768) was substituted and it was therefore concluded that EDD is an E3.

Few E3 genes have been cloned (only two from human) but others are likely to exist as ubiquitin-dependent proteolysis is involved in many cellular processes and targets many known proteins. Ubiquitin-mediated proteolysis is critical in the control of cell cycle progression, being responsible for the periodic destruction of key cell cycle regulators including cyclins (35–37) and cyclin-dependent kinase inhibitors (38, 39) and also targeting transcription factors (40–43), the tumor suppressor protein p53 (18) and cell-cell signalling components such as b-catenin (44). Disruption of the murine Itch locus, which encodes an E3, caused hyperplasia in lymphoid and gastrointestinal epithelial tissues and an abnormal inflammatory response (21) while mutations in E6-AP in humans result in neurological abnormalities, indicating critical, and perhaps tissue specific, roles for E3 proteins (45).

Although substrates for EDD and its rat and Drosophila homologs have yet to be defined, conservation between the central domain of EDD and that of HYD suggests that this region has an important function, perhaps in substrate recognition. For the yeast E3 Rsp5, substrate specificity is determined by the amino terminal domain and does not require the HECT domain (16). Alternatively, this region could be involved in the binding of as yet unknown E2 proteins that interact specifically with EDD. The mouse E3 Nedd4 has at least two distinct E2 binding domains, only one of which is within the HECT domain (15) while human E6-AP requires only the HECT domain for E2 recognition (46). As the protein produced from the truncated EDD construct still binds ubiquitin reversibly, at least some E2 recognition function is present in this carboxyl domain. Other possible functions of the conserved central domain include cellular localization or translocation between cytoplasm and nucleus, cofactor association or phosphorylation.

Although ubiquitination is clearly involved in steroid-responsive processes such as regulation of cell cycle progression, specific regulation of ubiquitin pathways by steroid hormones has not previously been reported. The precise role of EDD in progestin action is unknown, particularly whether it participates in those key early events that occur in response to this hormone and which are ultimately responsible for its effects on cell proliferation and differentiation. Progestin regulation of EDD mRNA, which requires de novo protein synthesis, is transient with maximal levels 3 to 4-fold above control observed at 6 h. This increase in EDD expression levels therefore precedes the increase in the S phase fraction of T-47D cells following ORG 2058 treatment under the same conditions, which typically occurs at 12 to 14 h (3) and hence is consistent with a possible role in control of cell cycle progression. Similar levels of EDD induction were observed in antiestrogen-arrested MCF-7 breast cancer cells treated with 17b-estradiol (not shown), suggesting this may be a generalized response to mitogens.

However, given that EDD is also expressed in non-progestin target tissues, a more widespread role than specifically mediating progestin effects is expected. Information on the biological role of HYD from mutagenesis studies in Drosophila (13) may ultimately give clues as to the function of EDD. The null hyd phenotype is lethal, as are severe mutations in the pupal or larval stages. Less severe mutations result in overgrowth (hyperplasia) of larval imaginal discs (the larval centres of cell proliferation that give rise to adult structures such as wings, legs and antennae), apparently caused by a failure to terminate cell proliferation when the discs reach their characteristic size, hence the definition of hyd as a tumor suppressor gene. Surviving adults are sterile due to germ cell defects, and interestingly, high expression levels of EDD and rat 100 kDa protein mRNA are seen in human and rat testes, suggesting a critical function in this organ.

Studies of a number of human homologues of Drosophila tumor suppressor genes strongly suggests that these genes have similar roles in both species in controlling cell proliferation, and that such genes can be important in human heritable and sporadic cancers, for example patched (47), mutations of which are linked to basal cell carcinoma, and discs large (45, 48), a target of the APC gene which is mutated in sporadic colorectal tumors and familial adenomatous polyposis coli. The possible involvement of EDD in human tumorigenesis and tumor progression is therefore of particular interest. The EDD gene locus at chromosome 8q22 is often disrupted in a variety of cancers, being deleted in adenocarcinoma of the ovary and lung (49, 50), hepatocellular carcinoma (51) and head and neck squamous cell carcinoma (52), amplified in many tumor types including gastrointestinal and primary breast cancers (53, 54) and involved in translocations in acute myeloid leukemia (55). Chromosome 8q22 is also a region affected in the human developmental disorder Klippel-Feil syndrome (56).

REFERENCES

1. Clarke, C. L., and Sutherland, R. L. (1990) Endocr. Rev. 11, 266–301
2. Dickson, R. B., and Lippman, M. E. (1995) Endocr Rev 16, 559–589
3. Musgrove, E. A., Lee, C. S. L., and Sutherland, R. L. (1991) Mol Cell Biol 11, 5032–5043
4. Musgrove, E. A., Swarbrick, A., Lee, C. S. L., Cornish, A. L., and Sutherland, R. L. (1998) Mol. Cell. Biol. In Press,
5. Prall, O. W. J., Sarcevic, B., Musgrove, E. A., Watts, C. K. W., and Sutherland, R. L. (1997) J. Biol. Chem. 272, 10882–10894
6. Lydon, J. P., DeMayo, F. J., Funk, C. R., Mani, S. K., Hughes, A. R., Montgomery Jr., C. A., Shyamala, G., Conneely, O. M., and O'Malley, B. W. (1995) Genes Dev. 9, 2266–2278
7. Sutherland, R. L., Prall, O. W. J., Watts, C. K. W., and Musgrove, E. A. (1998) J. Mamm. Gland Biol. Neoplasia 3, 63–71

8. Laidlaw, I. J., Clarke, R. B., Howell, A., Owen, A. W. M. C., Potten, C. S., and Anderson, E. (1995) *Endocrinology* 136, 164–171
9. Groshong, S. D., Owen, G. I., Grimison, B., Schauer, I. E., Todd, M. C., Langan, T. A., Sclafani, R. A., Lange, C. A., and Horwitz, K. B. (1997) *Mol. Endocrinol.* 11, 1593–1607.
10. Musgrove, E. A., Hamilton, J. A., Lee, C. S. L., Sweeney, K. J. E., Watts, C. K. W., and Sutherland, R. L. (1993) *Mol. Cell. Biol.* 13, 3577–3587
11. Liang, P., and Pardee, A. B. (1992) *Science* 257, 967–971
12. Hamilton, J. A., Callaghan, M. J., Sutherland, R. L., and Watts, C. K. W. (1997) *Mol. Endocrinol.* 11, 490–502
13. Mansfield, E., Hersperger, E., Biggs, J., and Shearn, A. (1994) *Dev. Biol.* 165, 507–526
14. Huibregtse, J. M., Scheffner, M., Beaudenon, S., and Howley, P. M. (1995) *Proc Natl Acad Sci U S A* 92, 5249
15. Hatakeyama, S., Jensen, J. P., and Weissman, A. M. (1997) *J Biol Chem* 272, 15085–15092
16. Huibregtse, J. M., Yang, J. C., and Beaudenon, S. L. (1997) *Proc. Natl. Acad. Sci. U S A* 94, 3656–3661
17. Huibregtse, J. M., Scheffner, M., and Howley, P. M. (1993) *Mol. Cell. Biol.* 13, 775–784
18. Scheffner, M., Huibregtse, J. M., Vierstra, R. D., and Howley, P. M. (1993) *Cell* 75, 495–505
19. Gu, J., Ren, K., Dubner, R., and Iadarola, M. J. (1994) *Mol Brain Res* 24, 77–88
20. Kumar, S., Harvey, K. F., Kinoshita, M, Copeland, N. G., Noda, M., and Jenkins, N. A. (1997) *Genomics* 40, 435–443
21. Perry, W. L., Hustad, C. M., Swing, D. A., O'Sullivan, T. N., Jenkins, N. A., and Copeland, N. G. (1998) *Nat. Genet.* 18, 143–146
22. Buckley, M. F., Sweeney, K. J. E., Hamilton, J. A., Sini, R. L., Manning, D. L., Nicholson, R. I., deFazio, A., Watts, C. K. W., Musgrove, E. A., and Sutherland, R. L. (1993) *Oncogene* 8, 2127–2133
23. Alexander, I. E., Clarke, C. L., Shine, J., and Sutherland, R. L. (1989) *Mol Endocrinol* 3, 1377–1386
24. Chan, Y.-L., Guttell, R., Noller, H. F., and Wool, I. G. (1984) *J Biol Chem* 259, 224–230
25. Hall, R. E., Lee, C. S. L., Alexander, I. E., Shine, J., Clarke, C. L., and Sutherland, R. L. (1990) *Int J Cancer* 46, 1081–1087
26. Muller, D., Rehbein, M., Baumeister, H., and Richter, D. (1992) *Nucleic Acids Res* 20, 1471–1475
27. Callen, D., Baker, E., Eyre, H. J., Chernos, J. E., Bell, J. A., and Sutherland, G. R. (1990) *Ann Genet* 33, 219–221
28. Scheffner, M., Nuber, U., and Huibregtse, J. M. (1995) *Nature* 373, 81–83
29. Kozak, M. (1987) *Nucleic Acids Res* 15, 8125–8132
30. Nefsky, B., and Beach, D. (1996) *EMBO J.* 15, 1301–1312
31. van Gool, A. J., Verhage, R., Swagemakers, S. M., van de Putte, P., Brouwer, J., Troelstra, C., Bootsma, D., and Hoeijmakers, J.H. (1994) *EMBO J.* 13, 5361–5369
32. Staub, O., Dho, S., Henry, P., Correa, J., Ishikawa, T., McGlade, J., and Rotin, D. (1996) *EMBO J.* 15, 2371–2380
33. Nagase, T., Miyajima, N., Tanaka, A., Sazuka, T., Seki, N., Sato, S., Tabata, S., Ishikawa, K., Kawarabayasi, Y., Kotani, H., et al. (1995) *DNA Res* 2, 37–43
34. Dingwall, C., and Laskey, R. A. (1991) *Trends Biochem Sci* 16, 478–481
35. Won, K. A., and Reed, S. I. (1996) *EMBO J.* 15, 4182–4193
36. Diehl, J. A., Zindy, F., and Sherr, C. J. (1997) *Genes Dev* 11, 957–972
37. King, R. W., Deshaies, R. J., Peters, J. M., and Kirschner, M. W. (1996) *Science* 274, 1652–1659
38. Benito, J., Martin-Castellanos, C., and Moreno, S. (1998) *EMBO J.* 17, 482–497
39. Pagano, M., Tam, S. W., Theodoras, A. M., Beer-Romero, P., Del Sal, G., Chau, V., Yew, P. R., Draetta, G. F., and Rolfe, M. (1995) *Science* 269, 682–685
40. Musti, A. M., Treier, M., Peverali, F. A., and Bohmann, D. (1996) *Biol. Chem.* 377, 619–624
41. Musti, A. M., Treier, M., and Bohmann, D. (1997) *Science* 275, 400–402
42. Palombella, V. J., Rando, O. J., Goldberg, A. L., and Maniatis, T. (1994) *Cell* 78, 773–785
43. Orian, A., Whiteside, S., Israel, A., Stancovski, I., Schwartz, A. L., and Ciechanover, A. (1995) *J. Biol. Chem.* 270, 21707–21714
44. Orford, K., Crockett, C., Jensen, J. P., Weissman, A. M., and Byers, S. W. (1997) *J. Biol. Clem.* 272, 24735–24738
45. Kishino, T., Lalande, M., and Wagstaff, J. (1997) *Nat Genet* 15, 70–73
46. Kumar, S., Kao, W. H., and Howley, P. M. (1997) *J. Biol. Chem.* 272, 13548–13554
47. Johnson, R. L., Rothman, A. L., Xie, J., Goodrich, L. V., Bare, J. W., Bonifas, J. M., Quinn, A. G., Myers, R. M., Cox, D. R., Epstein, E., Jr., and Scott, M. P. (1996) *Science* 272, 1668–1671
48. Matsuura, T., Sutcliffe, J. S., Fang, P., Galjaard, R. J., Jiang, Y. H., Benton, C. S., Rommens, J. M., and Beaudet, A. L. (1997) *Nat Genet* 15, 74–77
49. Mitelman, F., Mertens, F., and Johansson, B. (1997) *Nat. Genet.* 15, 417–474
50. Sato, S., Nakamura, Y., and Tsuchiya, E. (1994) *Cancer Res.* 54, 5652–5655
51. Piao, Z., Park, C., Park, J., and Kim, H. (1998) *Int. J. Cancer* 75, 29–33
52. Nawroz, H., van der Riet, P., Hruban, R. H., Koch, W., Ruppert, J. M., and Sidransky, D. (1994) *Cancer Res.* 54, 11152–11155
53. El-Rifai, W., Sarlomo-Rikala, M., Miettinen, M., Knuutila, S., and Andersson, L. C. (1996) *Cancer Res* 56, 3230–3233
54. Muleris, M., Almeida, A., Gerbault-Seureau, M., Malfoy, B., and Dutrillaux, B. (1994) *Genes Chromosomes Cancer* 10, 160–170
55. Erickson, P., Gao, J., Chang, K. S., Look, T., Whisenant, E., Raimondi, S., Lasher, R., Trujillo, J., Rowley, J., and Drabkin, H. (1992) *Blood* 80, 1825–1831
56. Clarke, R. A., Singh, S., McKenzie, H., Kearsley, J. H., and Yip, M. Y. (1995) *Am J Hum Genet* 57, 1364–1370

The abbreviations used in this specification are: DD-PCR, differential display polymerase chain reaction; DTT, dithiothreitol; EDD, E3 isolated by differential display; FISH, fluorescence in situ hybridization; GST, glutathione S-transferase; HECT, homologous to E6-AP carboxyl terminus; PAGE, polyacrylamide gel electrophoresis; PMSF, phenylmethylsulfonyl fluoride; PR, progesterone receptor; RACE, rapid amplification of cDNA ends.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An isolated nucleic acid comprising a nucleotide sequence selected from the group consisting of:
   (i) the nucleotide sequence set forth in SEQ ID NO: 3;
   (ii) the nucleotide sequence set forth in SEQ ID NO: 5;
   (iii) a nucleotide sequence that encodes the amino acid sequence set forth in SEQ ID NO: 4;
   (iv) a nucleotide sequence that encodes the amino acid sequence set forth in SEQ ID NO: 4 wherein cysteine is substituted for alanine at position 2768; and
   (v) a nucleotide sequence of human origin that encodes a polypeptide having a molecular weight of about 300 kDa as determined by SDS-polyacrylamide gel electrophoresis (SDS-PAGE) and comprising an amino acid sequence that is at least 95% identical to SEQ ID NO: 4 over its entire length wherein each difference between said amino acid sequence and SEQ ID NO: 4 does not reduce the ability of said polypeptide to bind ubiquitin or does not reduce the ability of said polypeptide to react with an antibody that binds to SEQ ID NO: 4.

2. The isolated nucleic acid according to claim 1 wherein the nucleotide sequence is expressed in a human tissue selected from the group consisting of: pancreas, skeletal muscle, placenta, heart, small intestine, ovary, testis, prostate, thymus, pituitary, kidney, uterus, stomach, lung, and brain.

3. The isolated nucleic acid according to claim 1 wherein the expression of the nucleotide sequence is enhanced in a human breast cancer cell compared to a healthy breast cell of humans.

4. The isolated nucleic acid according to claim 1 comprising the nucleotide sequence set forth in SEQ ID NO: 3.

5. The isolated nucleic acid according to claim 1 comprising the nucleotide sequence set forth in SEQ ID NO: 5.

6. The isolated nucleic acid according to claim 1 comprising a nucleotide sequence that encodes the amino acid sequence set forth in SEQ ID NO: 4.

7. The isolated nucleic acid according to claim 1 comprising a nucleotide sequence of human origin, wherein the expression of said sequence in a human cell is enhanced by progestin.

8. The isolated nucleic acid according to claim 1 wherein said nucleic acid comprises a nucleotide sequence of human origin that encodes a polypeptide having a molecular weight of about 300 kDa as determined by SDS-polyacrylamide gel electrophoresis (SDS-PAGE) and comprising an amino acid sequence that is at least 95% identity to SEQ ID NO: 4 over its entire length wherein each difference between said amino acid sequence and SEQ ID NO: 4 is a conservative amino acid substitution that does not reduce the ability of said polypeptide bind ubiquitin or does not reduce the ability of said polypeptide to react with an antibody that binds to SEQ ID NO: 4.

9. The isolated nucleic acid according to claim 1 wherein said nucleic acid encodes a polypeptide comprising an amino acid sequence that differs from SEQ ID NO: 4 by a single amino acid substitution.

* * * * *

SEQUENCE LISTING

<160> NUMBER OF SEQ ID NOS: 17

<210> SEQ ID NO 1
<211> LENGTH: 10
<212> TYPE: PRT
<213> ORGANISM: Homo sapiens

<400> SEQUENCE: 1

Met Thr Ser Ile His Phe Val Val His Pro
 1               5                  10

<210> SEQ ID NO 2
<211> LENGTH: 50
<212> TYPE: PRT
<213> ORGANISM: Homo sapiens

<400> SEQUENCE: 2

Met Thr Ser Ile His Phe Val Val His Pro Leu Pro Gly Thr Glu Asp
 1               5                  10                  15

Gln Leu Asn Asp Arg Leu Arg Glu Val Ser Glu Lys Leu Asn Lys Tyr
             20                  25                  30

Asn Leu Asn Ser His Pro Pro Leu Asn Val Leu Glu Gln Ala Thr Ile
         35                  40                  45

Lys Gln
     50

<210> SEQ ID NO 3
<211> LENGTH: 8391
<212> TYPE: DNA
<213> ORGANISM: Homo sapiens

<400> SEQUENCE: 3

| | | | | | |
|---|---|---|---|---|---|
| atgacgtcca | tccatttcgt | ggttcacccg | ctgccgggca | ccgaggacca | gctcaatgac | 60 |
| aggttacgag | aagtttctga | gaagctgaac | aaatataatt | taaacagcca | ccccccttg | 120 |
| aatgtattcc | aacaggctac | tattaaacag | tgtgtggtgg | gaccaaatca | tgctgccttt | 180 |
| cttcttgagg | atggtagagt | ttgcaggatt | ggttttcag | tacagccaga | cagattggaa | 240 |
| ttgggtaaac | ctgataataa | tgatgggtca | aagttgaaca | gcaactcggg | ggcagggagg | 300 |
| acgtcaaggc | ctggtaggac | aagcgactct | ccatggtttc | tctcaggttc | tgagactcta | 360 |
| ggcaggctgg | caggcaacac | cttaggaagc | cgctggagtt | ctggagtggg | tggaagtggt | 420 |
| ggaggatcct | ctggtaggtc | atcagctgga | gctcgagatt | cccgccggca | gactcgagtt | 480 |
| attcggacag | gacgggatcg | agggtctggg | cttttgggca | gtcagcccca | gccagttatt | 540 |
| ccagcatctg | tcattccaga | ggagctgatt | tcacaggccc | aagttgtttt | acaaggcaaa | 600 |
| tccagaagtg | tcattattcg | agaacttcag | agaacaaatc | ttgatgtgaa | ccttgctgta | 660 |
| aataatttac | ttagccggga | tgatgaagat | ggagatgatg | gggatgatac | agccagcgaa | 720 |
| tcttatttgg | ctggagagga | tcttatgtct | ctccttgatg | ccgacattca | ttctgcccac | 780 |
| ccaagtgtca | ttattgatgc | agatgccatg | ttttctgaag | acattagcta | ttttggttac | 840 |
| ccttcttttc | gtcgttcatc | actttccagg | ctaggctcat | ctcgagttct | ccttcttccc | 900 |
| ttagagagag | actctgagct | gttgcgtgaa | cgcgaatccg | ttttacgttt | acgtgaacga | 960 |
| aggtggcttg | atgagcctc | atttgataat | gaaggggtt | ctaccaagca | aggaaggaga | 1020 |
| gccaaacttg | ataagaagaa | tacacctgtt | caaagtccag | tatctctagg | agaagatttg | 1080 |

-continued

```
cagtggtggc ctgataagga tggaacaaaa ttcatctgta tggctctgta ttctgaactt   1140
ctggctgtca gcagtaaagg agaactttat cagtggaaat ggagtgaatc tgagccttac   1200
agaaatgccc agaatccttc attacatcat ccacgagcaa cattttgggg gttaaccaat   1260
gaaaagatag tcctcctgtc tgcaaatagc ataagagcaa ctgtagctac agaaaagaac   1320
aaggttgcta catgggtgga tgaaacttta agttctgtgg cttctaaatt agagcacact   1380
gctcagactt actctgaact tcaaggagag cggatagttt ctttacattg ctgtgccctt   1440
tacacctgcg ctcagctgga aaacagttta tattggtggg gtgtagttcc ttttagtcaa   1500
aggaagaaaa tgttagagaa agctagagca aaaaataaaa agcctaaatc cagtgctggt   1560
atttcttcaa tgccgaacat cactgttggt acccaggtat gcttgagaaa taatcctctt   1620
tatcatgctg gagcagttgc attttcaatt agtgctggga ttcctaaagt tggtgtctta   1680
atggagtcag tttggaatat gaatgacagc tgtagatttc aacttagatc tcctgaaagc   1740
ttgaaaaaca tggaaaaagc tagcaaaact actgaagcta agcctgaaag taagcaggag   1800
ccagtgaaaa cagaaatggg tcctccacca tctccagcat ccacgtgtag tgatgcatcc   1860
tcaattgcca gcagtgcatc aatgccatac aaacgacgac ggtcaacccc tgcaccaaaa   1920
gaagaggaaa aggtgaatga agagcagtgg tctcttcggg aagtggtttt tgtggaagat   1980
gtcaagaatg ttcctgttgg caaggtgcta aaagtagatg gtgcctatgt tgctgtaaaa   2040
tttccaggaa cctccagtaa tactaactgt cagaacagct ctggtccaga tgctgaccct   2100
tcttctctcc tgcaggattg taggttactt agaattgatg aattgcaggt tgtcaaaact   2160
ggtggaacac cgaaggttcc cgactgtttc caaaggactc ctaaaaagct ttgtataccct   2220
gaaaaaacag aaatattagc agtgaatgta gattccaaag gtgttcatgc tgttctgaag   2280
actggaaatt gggtgcgata ctgtatcttt gatcttgcta caggaaaagc agaacaggaa   2340
aataattttc ctacaagcag cattgctttc cttggtcaga atgagaggaa tgtagccatt   2400
ttcactgctg gacaggaatc tcccattatt cttcgagatg gaaatggtac catctaccca   2460
atggccaaag attgcatggg aggaataagg gatcccgatt ggctggatct tccacctatt   2520
agtagtcttg gaatgggtgt gcattcttta ataaatcttc ctgccaattc aacaatcaaa   2580
aagaaagctg ctgttatcat catggctgta gagaaacaaa ccttaatgca acacattctg   2640
cgctgtgact atgaggcctg tcgacaatat ctaatgaatc ttgagcaacg ttttttagag   2700
cagaatctac agatgctgca gacattcatc agccacagat gtgatggaaa tcgaaatatt   2760
ttgcatgctt gtgtatcagt ttgctttcca accagcaata aagaaactaa agaagaagag   2820
gaagcggagc gttctgaaag aaatacattt gcagaaaggc tttctgctgt tgaggccatt   2880
gcaaatgcaa tatcagttgt ttcaagtaat ggcccaggta tcgggctgg atcatcaagt   2940
agccgaagtt tgagattacg ggaaatgatg agacgttcgt tgagagcagc tggtttgggt   3000
agacatgaag ctggagcttc atccagtgac caccaggatc cagtttcacc ccccatagct   3060
ccccctagtt gggttcctga ccctcctgcg atggatcctg atggtgacat tgattttatc   3120
ctggcccccg ctgtgggatc tcttaccaca gcagcaaccg gtactggtca aggaccaagc   3180
acctccacta ttccaggtcc ttccacagag ccatctgtag tagaatccaa ggatcgaaag   3240
gcgaatgctc attttatatt gaaattgtta tgtgacagtg tggttctcca gccctatcta   3300
cgagaacttc tttctgccaa ggatgcaaga gggatgaccc catttatgtc agctgtaagt   3360
ggccgagctt atcctgctgc aattaccatc ttagaaactg ctcagaaaat tgcaaaagct   3420
gaaatatcct caagtgaaaa agaggaagat gtattcatgg aatggtttg cccatcaggt   3480
```

-continued

```
accaaccctg atgactctcc tttatatgtt ttatgttgta atgacacttg cagttttaca   3540
tggactggag cagagcacat taaccaggat attttttgagt gtcgaacttg tggcttgctg   3600
gagtcactgt gttgttgtac ggaatgtgca ggggtttgtc ataaaggtca tgattggaaa   3660
ctcaaacgga catcaccaac agcctactgt gactgttggg agaaatgtaa atgtaaaact   3720
cttattgctg gacagaaatc tgctcgtctt gatctacttt atcgcctgct cactgctact   3780
aatctggtta ctctgccaaa cagcagggga gagcacctct tactattctt agtacagaca   3840
gtcgcaaggc agacggtgga gcattgtcaa tacaggccac ctcgaatcag ggaagatcgt   3900
aaccgaaaaa cagccagtcc tgaagattca gatatgccag atcatgattt agagcctcca   3960
agatttgccc agcttgcatt ggagcgtgtt ctacaggact ggaatgcctt gaaatctatg   4020
attatgtttg ggtcgcagga gaataaagac cctcttagtg ccagcagtag aataggccat   4080
cttttgccag aagagcaagt atacctcaat cagcaaagtg gcacaattcg gctggactgt   4140
ttcactcatt gccttatagt taagtgtaca gcagatattt tgcttttaga tactctacta   4200
ggtacactag tgaaagaact ccaaaacaaa tatacacctg gacgtagaga agaagctatt   4260
gctgtgacaa tgaggtttct acgttcagtg gcaagagttt ttgttattct gagtgtggaa   4320
atggcttcat ccaaaaagaa aaacaacttt attccacagc caattggaaa atgcaagcgt   4380
gtattccaag cattgctacc ttacgctgtg aagaattgt gcaacgtagc agagtcactg   4440
attgttcctg tcagaatggg gattgctcgt ccaactgcac catttaccct ggctagtact   4500
agcatagatg ccatgcaggg cagtgaagaa ttattttcag tggaaccact gccaccacga   4560
ccatcatctg atcagtctag cagctccagt cagtctcagt catcctacat catcaggaat   4620
ccacagcaga ggcgcatcag ccagtcacag cccgttcggg gcagagatga agaacaggat   4680
gatattgttt cagcagatgt ggaagaggtt gaggtggtgg agggtgtggc tggagaagag   4740
gatcatcatg atgaacagga agaacacggg gaagaaaatg ctgaggcaga gggacaacat   4800
gatgagcatg atgaagacgg gagtgatatg gagctggact tgttagcagc agcagaaaca   4860
gaaagtgata gtgaaagtaa ccacagcaac caagataatg ctagtgggcg cagaagcgtt   4920
gtcactgcag caactgctgg ttcagaagca ggagcaagca gtgttcctgc cttcttttct   4980
gaagatgatt ctcaatcgaa tgactcaagt gattctgata gcagtagtag tcagagtgac   5040
gacatagaac aggagaccct tatgcttgat gagccattag aaagaaccac aaatagctcc   5100
catgccaatg tgctgcccca agctcccgt tcaatgcagt gggctgtccg caacaccctg   5160
catcagcgag cagccagtac agcccctcc agtacatcta caccagcagc aagttcagcg   5220
ggtttgattt atattgatcc ttcaaactta cgccggagtg gtaccatcag tacaagtgct   5280
gcagctgcag cagctgcttt ggaagctagc aacgccagca gttacctaac atctgcaagc   5340
agtttagcca gggcttacag catgtcatta gacaaatcat cggacttgat gggccttatt   5400
cctaagtata atcacctagt atactctcag attccagcag ctgtgaaatt gacttaccaa   5460
gatgcagtaa acttacagaa ctatgtagaa gaaaagctta ttcccacttg gaactggatg   5520
gtcagtatta tggattctac tgaagctcaa ttacgttatg gttctgcatt agcatctgct   5580
ggtgatcctg gacatccaaa tcatcctctt cacgcttctc agaattcagc gagaagagag   5640
aggatgactg cgcgagaaga agctagctta cgaacacttg aaggcagacg acgtgccacc   5700
ttgcttagcg cccgtcaagg aatgatgtct gcacgaggag acttcctaaa ttatgctctg   5760
tctctaatgc ggtctcataa tgatgagcat tctgatgttc ttccagtttt ggatgtttgc   5820
```

-continued

```
tcattgaagc atgtggcata tgtttttcaa gcacttatat actggattaa ggcaatgaat    5880
cagcagacaa cattggatac acctcaacta gaacgcaaaa ggacgcgaga actcttggaa    5940
ctgggtattg ataatgaaga ttcagaacat gaaaatgatg atgacaccaa tcaaagtgct    6000
actttgaatg ataaggatga tgactctctt cctgcagaaa ctggccaaaa ccatccattt    6060
ttccgacgtt cagactccat gacattcctt gggtgtatac ccccaaatcc atttgaagtg    6120
cctctggctg aagccatccc cttggctgat cagcccacatc tgttgcagcc aaatgctaga    6180
aaggaggatc tttttggccg tccaagtcag ggtctttatt cttcatctgc cagtagtggg    6240
aaatgtttaa tggaggttac agtggataga aactgcctag aggttcttcc aacaaaaatg    6300
tcttatgctg ccaatctgaa aaatgtaatg aacatgcaaa accggcaaaa aagaagggg    6360
aaggaacagc ccgtgctgcc agaagaaact gagagttcaa aaccagggcc atctgctcat    6420
gatcttgctg cacaattaaa aagtagctta ctagcagaaa taggacttac tgaaagtgaa    6480
gggccacctc tcacatcttt caggccacag tgtagcttta tgggaatggt tctttcccat    6540
gatatgctgc taggacgttg gcgccttttct ttagaactgt tcggcagggt attcatggaa    6600
gatgttggag cagaacctgg atcaatccta actgaattgg gtggttttga ggtaaaagaa    6660
tcgaaattcc gcagagaaat ggaaaaactg agaaaccagc agtcaagaga tttgtcacta    6720
gaggttgatc gggatcgaga tcttctcatt cagcagacta tgaggcagct taacaatcac    6780
tttggtcgaa gatgtgctac tataccaatg gctgtacaca gagtaaaagt cacatttaag    6840
gatgagccag gagagggcag tggtgtagca cgaagttttt atacagccat gcacaagca    6900
ttttttatcaa atgaaaaatt gccaaatcta gagtgtatcc aaaatgccaa caaaggcacc    6960
cacacaagtt taatgcagag attaaggaac cgaggagaga gagaccggga aagggagaga    7020
gaaagggaaa tgaggaggag tagtggtttg cgagcaggtt ctcggaggga ccgggataga    7080
gactttagaa gacagctttc catcgacact aggcccttta gaccagcctc tgaagggaat    7140
cctagcgatg atcctgagcc tttgccagca catcggcagg acttggaga gaggctttat    7200
cctcgtgtac aagcaatgca accagcattt gcaagtaaaa tcactggcat gttgttggat    7260
tatcccagct cagctgcttc tcttctagca agtgaggatt ctctgagagc aagagtggat    7320
gaggccatgg aactcattat tgcacatgga cgggaaaatg gagctgatag tatcctggat    7380
cttggattag tagactcctc agaaaaggta cagcaggaaa accgaaagcg ccatggctct    7440
agtcgaagtg tagtagatat ggatttagat gatacagatg atggtgatga caatgcccct    7500
ttgttttacc aacctgggaa aagaggattt tatactccaa ggcctggcaa gaacacagaa    7560
gcaaggttga attgtttcag aaacattggc aggattcttg gactatgtct gttacagaat    7620
gaactctgtc ctatcacatt gaatagacat gtaattaaag tattgcttgg tagaaaaagtc    7680
aattggcatg attttgcttt ttttgatcct gtaatgtatg agagtttgcg gcaactaatc    7740
ctcgcgtctc agagttcaga tgctgatgct gttttctcag caatgattt ggcatttgca    7800
attgacctgt gtaaagaaga aggtggagga caggttgaac tcattcctaa tggtgtaaag    7860
agaccagtca ctccacagaa tgtatatgag tatgtgcgga agacgcaga acacagaatg    7920
ttggtagttg cagaacagcc cttacatgca atgaggaaag gtctactaga tgtgcttcca    7980
aaaaattcat tagaagattt aacggcagaa gatttaggc ttttggtaaa tggctgcggt    8040
gaagtcaatg tgcaaatgct gatcagtttt acctctttca atgatgaatc aggagaaaat    8100
gctgagaagc ttctgcagtt caagcgttgg ttctggtcaa tagtagagaa gatgagcatg    8160
acagaacgac aagatcttgt ttactttttgg acatcaagcc catcactgcc agccagtgaa    8220
```

-continued

```
gaaggattcc agcctatgcc ctcaatcaca ataagaccac cagatgacca acatcttcct    8280
actgcaaata cttgcatttc tcgactttac gtcccactct attcctctaa acagattctc    8340
aaacagaaat tgttactcgc cattaagacc aagaattttg gttttgtgta g             8391
```

<210> SEQ ID NO 4
<211> LENGTH: 2799
<212> TYPE: PRT
<213> ORGANISM: Homo sapiens

<400> SEQUENCE: 4

```
Met Thr Ser Ile His Phe Val Val His Pro Leu Pro Gly Thr Glu Asp
 1               5                  10                  15

Gln Leu Asn Asp Arg Leu Arg Glu Val Ser Glu Lys Leu Asn Lys Tyr
            20                  25                  30

Asn Leu Asn Ser His Pro Pro Leu Asn Val Leu Glu Gln Ala Thr Ile
        35                  40                  45

Lys Gln Cys Val Val Gly Pro Asn His Ala Ala Phe Leu Leu Glu Asp
    50                  55                  60

Gly Arg Val Cys Arg Ile Gly Phe Ser Val Gln Pro Asp Arg Leu Glu
65                  70                  75                  80

Leu Gly Lys Pro Asp Asn Asn Asp Gly Ser Lys Leu Asn Ser Asn Ser
                85                  90                  95

Gly Ala Gly Arg Thr Ser Arg Pro Gly Arg Thr Ser Asp Ser Pro Trp
            100                 105                 110

Phe Leu Ser Gly Ser Glu Thr Leu Gly Arg Leu Ala Gly Asn Thr Leu
        115                 120                 125

Gly Ser Arg Trp Ser Ser Val Gly Gly Ser Gly Gly Ser Ser
    130                 135                 140

Gly Arg Ser Ser Ala Gly Ala Arg Asp Ser Arg Arg Gln Thr Arg Val
145                 150                 155                 160

Ile Arg Thr Gly Arg Asp Arg Gly Ser Gly Leu Leu Gly Ser Gln Pro
                165                 170                 175

Gln Pro Val Ile Pro Ala Ser Val Ile Pro Glu Glu Leu Ile Ser Gln
            180                 185                 190

Ala Gln Val Val Leu Gln Gly Lys Ser Arg Ser Val Ile Ile Arg Glu
        195                 200                 205

Leu Gln Arg Thr Asn Leu Asp Val Asn Leu Ala Val Asn Asn Leu Leu
    210                 215                 220

Ser Arg Asp Asp Glu Asp Gly Asp Asp Gly Asp Asp Thr Ala Ser Glu
225                 230                 235                 240

Ser Tyr Leu Ala Gly Glu Asp Leu Met Ser Leu Leu Asp Ala Asp Ile
                245                 250                 255

His Ser Ala His Pro Ser Val Ile Ile Asp Ala Asp Ala Met Phe Ser
            260                 265                 270

Glu Asp Ile Ser Tyr Phe Gly Tyr Pro Ser Phe Arg Arg Ser Ser Leu
        275                 280                 285

Ser Arg Leu Gly Ser Ser Arg Val Leu Leu Leu Pro Leu Glu Arg Asp
    290                 295                 300

Ser Glu Leu Leu Arg Glu Arg Glu Ser Val Leu Arg Leu Arg Glu Arg
305                 310                 315                 320

Arg Trp Leu Asp Gly Ala Ser Phe Asp Asn Glu Arg Gly Ser Thr Ser
                325                 330                 335

Lys Glu Gly Glu Pro Asn Leu Asp Lys Lys Asn Thr Pro Val Gln Ser
```

-continued

```
            340                 345                 350
Pro Val Ser Leu Gly Glu Asp Leu Gln Trp Trp Pro Asp Lys Asp Gly
            355                 360                 365
Thr Lys Phe Ile Cys Ile Gly Ala Leu Tyr Ser Glu Leu Leu Ala Val
            370                 375                 380
Ser Ser Lys Gly Glu Leu Tyr Gln Trp Lys Trp Ser Glu Ser Glu Pro
385                 390                 395                 400
Tyr Arg Asn Ala Gln Asn Pro Ser Leu His His Pro Arg Ala Thr Phe
                        405                 410                 415
Leu Gly Leu Thr Asn Glu Lys Ile Val Leu Leu Ser Ala Asn Ser Ile
            420                 425                 430
Arg Ala Thr Val Ala Thr Glu Asn Asn Lys Val Ala Thr Trp Val Asp
            435                 440                 445
Glu Thr Leu Ser Ser Val Ala Ser Lys Leu Glu His Thr Ala Gln Thr
            450                 455                 460
Tyr Ser Glu Leu Gln Gly Glu Arg Ile Val Ser Leu His Cys Cys Ala
465                 470                 475                 480
Leu Tyr Thr Cys Ala Gln Leu Glu Asn Ser Leu Tyr Trp Trp Gly Val
                        485                 490                 495
Val Pro Phe Ser Gln Arg Lys Lys Met Leu Glu Lys Ala Arg Ala Lys
            500                 505                 510
Asn Lys Lys Pro Lys Ser Ser Ala Gly Ile Ser Ser Met Pro Asn Ile
            515                 520                 525
Thr Val Gly Thr Gln Val Cys Leu Arg Asn Asn Pro Leu Tyr His Ala
            530                 535                 540
Gly Ala Val Ala Phe Ser Ile Ser Ala Gly Ile Pro Lys Val Gly Val
545                 550                 555                 560
Leu Met Glu Ser Val Trp Asn Met Asn Asp Ser Cys Arg Phe Gln Leu
                        565                 570                 575
Arg Ser Pro Glu Ser Leu Lys Asn Met Glu Lys Ala Ser Lys Thr Thr
            580                 585                 590
Glu Ala Lys Pro Glu Ser Lys Gln Glu Pro Val Lys Thr Glu Met Gly
            595                 600                 605
Pro Pro Pro Ser Pro Ala Ser Thr Cys Ser Asp Ala Ser Ser Ile Ala
            610                 615                 620
Ser Ser Ala Ser Met Pro Tyr Lys Arg Arg Ser Thr Pro Ala Pro
625                 630                 635                 640
Lys Glu Glu Glu Lys Val Asn Glu Glu Gln Trp Ser Leu Arg Glu Val
                        645                 650                 655
Val Phe Val Glu Asp Val Lys Asn Val Pro Val Gly Lys Val Leu Lys
            660                 665                 670
Val Asp Gly Ala Tyr Val Ala Val Lys Phe Pro Gly Thr Ser Ser Asn
            675                 680                 685
Thr Asn Cys Gln Asn Ser Ser Gly Pro Asp Ala Asp Pro Ser Ser Leu
            690                 695                 700
Leu Gln Asp Cys Arg Leu Leu Arg Ile Asp Glu Leu Gln Val Val Lys
705                 710                 715                 720
Thr Gly Gly Thr Pro Lys Val Pro Asp Cys Phe Gln Arg Thr Pro Lys
                        725                 730                 735
Lys Leu Cys Ile Pro Glu Lys Thr Glu Ile Leu Ala Val Asn Val Asp
            740                 745                 750
Ser Lys Gly Val His Ala Val Leu Lys Thr Gly Asn Trp Val Arg Tyr
            755                 760                 765
```

-continued

```
Cys Ile Phe Asp Leu Ala Thr Gly Lys Ala Glu Gln Glu Asn Asn Phe
    770                 775                 780
Pro Thr Ser Ser Ile Ala Phe Leu Gly Gln Asn Glu Arg Asn Val Ala
785                 790                 795                 800
Ile Phe Thr Ala Gly Gln Glu Ser Pro Ile Ile Leu Arg Asp Gly Asn
                    805                 810                 815
Gly Thr Ile Tyr Pro Met Ala Lys Asp Cys Met Gly Ile Arg Asp
                820                 825                 830
Pro Asp Trp Leu Asp Leu Pro Pro Ile Ser Ser Leu Gly Met Gly Val
                835                 840                 845
His Ser Leu Ile Asn Leu Pro Ala Asn Ser Thr Ile Lys Lys Lys Ala
    850                 855                 860
Ala Val Ile Ile Met Ala Val Glu Lys Gln Thr Leu Met Gln His Ile
865                 870                 875                 880
Leu Arg Cys Asp Tyr Glu Ala Cys Arg Gln Tyr Leu Met Asn Leu Glu
                    885                 890                 895
Gln Ala Val Val Leu Glu Gln Asn Leu Gln Met Leu Gln Thr Phe Ile
                900                 905                 910
Ser His Arg Cys Asp Gly Asn Arg Asn Ile Leu His Ala Cys Val Ser
    915                 920                 925
Val Cys Phe Pro Thr Ser Asn Lys Glu Thr Lys Glu Glu Glu Glu Ala
    930                 935                 940
Glu Arg Ser Glu Arg Asn Thr Phe Ala Glu Arg Leu Ser Ala Val Glu
945                 950                 955                 960
Ala Ile Ala Asn Ala Ile Ser Val Val Ser Ser Asn Gly Pro Gly Asn
                    965                 970                 975
Arg Ala Gly Ser Ser Ser Arg Ser Leu Arg Leu Arg Glu Met Met
                980                 985                 990
Arg Arg Ser Leu Arg Ala Ala Gly Leu Gly Arg His Glu Ala Gly Ala
    995                 1000                1005
Ser Ser Ser Asp His Gln Asp Pro Val Ser Pro Ile Ala Pro Pro
    1010                1015                1020
Ser Trp Val Pro Asp Pro Pro Ala Met Asp Pro Asp Gly Asp Ile Asp
1025                1030                1035                1040
Phe Ile Leu Ala Pro Ala Val Gly Ser Leu Thr Thr Ala Ala Thr Gly
                    1045                1050                1055
Thr Gly Gln Gly Pro Ser Thr Ser Thr Ile Pro Gly Pro Ser Thr Glu
                1060                1065                1070
Pro Ser Val Val Glu Ser Lys Asp Arg Lys Ala Asn Ala His Phe Ile
    1075                1080                1085
Leu Lys Leu Leu Cys Asp Ser Val Val Leu Gln Pro Tyr Leu Arg Glu
    1090                1095                1100
Leu Leu Ser Ala Lys Asp Ala Arg Gly Met Thr Pro Phe Met Ser Ala
1105                1110                1115                1120
Val Ser Gly Arg Ala Tyr Pro Ala Ala Ile Thr Ile Leu Glu Thr Ala
                    1125                1130                1135
Gln Lys Ile Ala Lys Ala Glu Ile Ser Ser Glu Lys Glu Glu Asp
                1140                1145                1150
Val Phe Met Gly Met Val Cys Pro Ser Gly Thr Asn Pro Asp Asp Ser
    1155                1160                1165
Pro Leu Tyr Val Leu Cys Cys Asn Asp Thr Cys Ser Phe Thr Trp Thr
    1170                1175                1180
```

```
Gly Ala Glu His Ile Asn Gln Asp Ile Phe Glu Cys Arg Thr Cys Gly
1185                1190                1195                1200

Leu Leu Glu Ser Leu Cys Cys Thr Glu Cys Ala Arg Val Cys His
            1205                1210                1215

Lys Gly His Asp Cys Lys Leu Lys Arg Thr Ser Pro Thr Ala Tyr Cys
        1220                1225                1230

Asp Cys Trp Glu Lys Cys Lys Cys Lys Thr Leu Ile Ala Gly Gln Lys
        1235                1240                1245

Ser Ala Arg Leu Asp Leu Leu Tyr Arg Leu Leu Thr Ala Thr Asn Leu
        1250                1255                1260

Val Thr Leu Pro Asn Ser Arg Gly Glu His Leu Leu Leu Phe Leu Val
1265                1270                1275                1280

Gln Thr Val Ala Arg Gln Thr Val Glu His Cys Gln Tyr Arg Pro Pro
                1285                1290                1295

Arg Ile Arg Glu Asp Arg Asn Arg Lys Thr Ala Ser Pro Glu Asp Ser
            1300                1305                1310

Asp Met Pro Asp His Asp Leu Glu Pro Pro Arg Phe Ala Gln Leu Ala
            1315                1320                1325

Leu Glu Arg Val Leu Gln Asp Trp Asn Ala Leu Lys Ser Met Ile Met
        1330                1335                1340

Phe Gly Ser Gln Glu Asn Lys Asp Pro Leu Ser Ala Ser Ser Arg Ile
1345                1350                1355                1360

Gly His Leu Leu Pro Glu Glu Gln Val Tyr Leu Asn Gln Gln Ser Gly
                1365                1370                1375

Thr Ile Arg Leu Asp Cys Phe Thr His Cys Leu Ile Val Lys Cys Thr
            1380                1385                1390

Ala Asp Ile Leu Leu Leu Asp Thr Leu Leu Gly Thr Leu Val Lys Glu
            1395                1400                1405

Leu Gln Asn Lys Tyr Thr Pro Gly Arg Arg Glu Glu Ala Ile Ala Val
        1410                1415                1420

Thr Met Arg Phe Leu Arg Ser Val Ala Arg Val Phe Val Ile Leu Ser
1425                1430                1435                1440

Val Glu Met Ala Ser Ser Lys Lys Lys Asn Asn Phe Ile Pro Gln Pro
                1445                1450                1455

Ile Gly Lys Cys Lys Arg Val Phe Gln Ala Leu Leu Pro Tyr Ala Val
                1460                1465                1470

Glu Glu Leu Cys Asn Val Ala Glu Ser Leu Ile Val Pro Val Arg Met
            1475                1480                1485

Gly Ile Ala Arg Pro Thr Ala Pro Phe Thr Leu Ala Ser Thr Ser Ile
        1490                1495                1500

Asp Ala Met Gln Gly Ser Glu Glu Leu Phe Ser Val Glu Pro Leu Pro
1505                1510                1515                1520

Pro Arg Pro Ser Ser Asp Gln Ser Ser Ser Ser Gln Ser Gln Ser
            1525                1530                1535

Ser Tyr Ile Ile Arg Asn Pro Gln Gln Arg Arg Ile Ser Gln Ser Gln
        1540                1545                1550

Pro Val Arg Gly Arg Asp Glu Glu Gln Asp Ile Val Ser Ala Asp
        1555                1560                1565

Val Glu Glu Val Glu Val Val Glu Gly Val Ala Gly Glu Glu Asp His
        1570                1575                1580

His Asp Glu Gln Glu Glu His Gly Glu Glu Asn Ala Glu Ala Glu Gly
1585                1590                1595                1600

Gln His Asp Glu His Asp Glu Asp Gly Ser Asp Met Glu Leu Asp Leu
```

-continued

```
                1605                1610                1615

Leu Ala Ala Ala Glu Thr Glu Ser Asp Ser Glu Ser Asn His Ser Asn
            1620                1625                1630

Gln Asp Asn Ala Ser Gly Arg Arg Ser Val Val Thr Ala Ala Thr Ala
            1635                1640                1645

Gly Ser Glu Ala Gly Ala Ser Ser Val Pro Ala Phe Phe Ser Glu Asp
            1650                1655                1660

Asp Ser Gln Ser Asn Asp Ser Ser Asp Ser Asp Ser Ser Ser Ser Gln
1665                1670                1675                1680

Ser Asp Asp Ile Glu Gln Glu Thr Phe Met Leu Asp Glu Pro Leu Glu
            1685                1690                1695

Arg Thr Thr Asn Ser Ser His Ala Asn Gly Ala Ala Gln Ala Pro Arg
            1700                1705                1710

Ser Met Gln Trp Ala Val Arg Asn Thr Gln His Gln Arg Ala Ala Ser
            1715                1720                1725

Thr Ala Pro Ser Ser Thr Ser Thr Pro Ala Ala Ser Ala Gly Leu
            1730                1735                1740

Ile Tyr Ile Asp Pro Ser Asn Leu Arg Arg Ser Gly Thr Ile Ser Thr
1745                1750                1755                1760

Ser Ala Ala Ala Ala Ala Ala Leu Glu Ala Ser Asn Ala Ser Ser
            1765                1770                1775

Tyr Leu Thr Ser Ala Ser Ser Leu Ala Arg Ala Tyr Ser Ile Val Ile
            1780                1785                1790

Arg Gln Ile Ser Asp Leu Met Gly Leu Ile Pro Lys Tyr Asn His Leu
            1795                1800                1805

Val Tyr Ser Gln Ile Pro Ala Ala Val Lys Leu Thr Tyr Gln Asp Ala
            1810                1815                1820

Val Asn Leu Gln Asn Tyr Val Glu Glu Lys Leu Ile Pro Thr Trp Asn
1825                1830                1835                1840

Trp Met Val Ser Ile Met Asp Ser Thr Glu Ala Gln Leu Arg Tyr Gly
            1845                1850                1855

Ser Ala Leu Ala Ser Ala Gly Asp Pro Gly His Pro Asn His Pro Leu
            1860                1865                1870

His Ala Ser Gln Asn Ser Ala Arg Arg Glu Arg Met Thr Ala Arg Glu
            1875                1880                1885

Glu Ala Ser Leu Arg Thr Leu Glu Gly Arg Arg Arg Ala Thr Leu Leu
            1890                1895                1900

Ser Ala Arg Gln Gly Met Met Ser Ala Arg Gly Asp Phe Leu Asn Tyr
1905                1910                1915                1920

Ala Leu Ser Leu Met Arg Ser His Asn Asp Glu His Ser Asp Val Leu
            1925                1930                1935

Pro Val Leu Asp Val Cys Ser Leu Lys His Val Ala Tyr Val Phe Gln
            1940                1945                1950

Ala Leu Ile Tyr Trp Ile Lys Ala Met Asn Gln Gln Thr Thr Leu Asp
            1955                1960                1965

Thr Pro Gln Leu Glu Arg Lys Arg Thr Arg Glu Leu Leu Glu Leu Gly
            1970                1975                1980

Ile Asp Asn Glu Asp Ser Glu His Glu Asn Asp Asp Thr Asn Gln
1985                1990                1995                2000

Ser Ala Thr Leu Asn Asp Lys Asp Asp Asp Ser Leu Pro Ala Glu Thr
            2005                2010                2015

Gly Gln Asn His Pro Phe Phe Arg Arg Ser Asp Ser Met Thr Phe Leu
            2020                2025                2030
```

-continued

```
Gly Cys Ile Pro Pro Asn Pro Phe Glu Val Pro Leu Ala Glu Ala Ile
            2035                2040                2045

Pro Leu Ala Asp Gln Pro His Leu Leu Gln Pro Asn Ala Arg Lys Glu
        2050                2055                2060

Asp Leu Phe Gly Arg Pro Ser Gln Gly Leu Tyr Ser Ser Ser Ala Ser
2065                2070                2075                2080

Ser Gly Lys Cys Leu Met Glu Val Thr Val Asp Arg Asn Cys Leu Glu
            2085                2090                2095

Val Leu Pro Thr Lys Met Ser Tyr Ala Ala Asn Leu Lys Asn Val Met
        2100                2105                2110

Asn Met Gln Asn Arg Gln Lys Lys Glu Gly Glu Glu Gln Pro Val Leu
            2115                2120                2125

Pro Glu Glu Thr Glu Ser Ser Lys Pro Gly Pro Ser Ala His Asp Leu
        2130                2135                2140

Ala Ala Gln Leu Lys Ser Ser Leu Leu Ala Glu Ile Gly Leu Thr Glu
2145                2150                2155                2160

Ser Glu Gly Pro Pro Leu Thr Ser Phe Arg Pro Gln Cys Ser Phe Met
            2165                2170                2175

Gly Met Val Ile Ser His Asp Met Leu Leu Gly Arg Trp Arg Leu Ser
            2180                2185                2190

Leu Glu Leu Phe Gly Arg Val Phe Met Glu Asp Val Gly Ala Glu Pro
            2195                2200                2205

Gly Ser Ile Leu Thr Glu Leu Gly Gly Phe Glu Val Lys Glu Ser Lys
        2210                2215                2220

Phe Arg Arg Glu Met Glu Lys Leu Arg Asn Gln Gln Ser Arg Asp Leu
2225                2230                2235                2240

Ser Leu Glu Val Asp Arg Asp Arg Asp Leu Leu Ile Gln Gln Thr Met
            2245                2250                2255

Arg Gln Leu Asn Asn His Phe Gly Arg Arg Cys Ala Thr Thr Pro Met
            2260                2265                2270

Ala Val His Arg Val Lys Val Thr Phe Lys Asp Glu Pro Gly Glu Gly
            2275                2280                2285

Ser Gly Val Ala Arg Ser Phe Tyr Thr Ala Ile Ala Gln Ala Phe Leu
        2290                2295                2300

Ser Asn Glu Lys Leu Pro Asn Leu Glu Cys Ile Gln Asn Ala Asn Lys
2305                2310                2315                2320

Gly Thr His Thr Ser Leu Met Gln Arg Leu Arg Asn Arg Gly Glu Arg
            2325                2330                2335

Asp Arg Glu Arg Glu Arg Glu Arg Glu Met Arg Arg Ser Ser Gly Leu
            2340                2345                2350

Arg Ala Gly Ser Arg Arg Asp Arg Asp Arg Asp Phe Arg Arg Gln Leu
        2355                2360                2365

Ser Ile Asp Thr Arg Pro Phe Arg Pro Ala Ser Glu Gly Asn Pro Ser
        2370                2375                2380

Asp Asp Pro Glu Pro Leu Pro Ala His Arg Gln Ala Leu Gly Glu Arg
2385                2390                2395                2400

Leu Tyr Pro Arg Val Gln Ala Met Gln Pro Ala Phe Ala Ser Lys Ile
            2405                2410                2415

Thr Gly Met Leu Leu Glu Leu Ser Pro Ala Gln Leu Leu Leu Leu Leu
        2420                2425                2430

Ala Ser Glu Asp Ser Leu Arg Ala Arg Val Asp Glu Ala Met Glu Leu
            2435                2440                2445
```

```
Ile Ile Ala His Gly Arg Glu Asn Gly Ala Asp Ser Ile Leu Asp Leu
    2450                2455                2460

Gly Leu Val Asp Ser Ser Glu Lys Val Gln Gln Glu Asn Arg Lys Arg
2465                2470                2475                2480

His Gly Ser Ser Arg Ser Val Val Asp Met Asp Leu Asp Thr Asp
                2485                2490                2495

Asp Gly Asp Asp Asn Ala Pro Leu Phe Tyr Gln Pro Gly Lys Arg Gly
        2500                2505                2510

Phe Tyr Thr Pro Arg Pro Gly Lys Asn Thr Glu Ala Arg Leu Asn Cys
            2515                2520                2525

Phe Arg Asn Ile Gly Arg Ile Leu Gly Leu Cys Leu Leu Gln Asn Glu
        2530                2535                2540

Leu Cys Pro Ile Thr Leu Asn Arg His Val Ile Lys Val Leu Leu Gly
2545                2550                2555                2560

Arg Lys Val Asn Trp His Asp Phe Ala Phe Phe Asp Pro Val Met Tyr
                2565                2570                2575

Glu Ser Leu Arg Gln Leu Ile Leu Ala Ser Gln Ser Ser Asp Ala Asp
            2580                2585                2590

Ala Val Phe Ser Ala Met Asp Leu Ala Phe Ala Ile Asp Leu Cys Lys
        2595                2600                2605

Glu Glu Gly Gly Gly Gln Val Glu Leu Ile Pro Asn Gly Val Asn Ile
    2610                2615                2620

Pro Val Thr Pro Gln Asn Val Tyr Glu Tyr Val Arg Lys Tyr Ala Glu
2625                2630                2635                2640

His Arg Met Leu Val Val Ala Glu Gln Pro Leu His Ala Met Arg Lys
                2645                2650                2655

Gly Leu Leu Asp Val Leu Pro Lys Asn Ser Leu Glu Asp Leu Thr Ala
            2660                2665                2670

Glu Asp Phe Arg Leu Leu Val Asn Gly Cys Gly Glu Val Asn Val Gln
        2675                2680                2685

Met Leu Ile Ser Phe Thr Ser Phe Asn Asp Glu Ser Gly Glu Asn Ala
    2690                2695                2700

Glu Lys Leu Leu Gln Phe Lys Arg Trp Phe Trp Ser Ile Val Glu Lys
2705                2710                2715                2720

Met Ser Met Thr Glu Arg Gln Asp Leu Val Tyr Phe Trp Thr Ser Ser
                2725                2730                2735

Pro Ser Leu Pro Ala Ser Glu Glu Gly Phe Gln Pro Met Pro Ser Ile
            2740                2745                2750

Thr Ile Arg Pro Pro Asp Asp Gln His Leu Pro Thr Ala Asn Thr Cys
        2755                2760                2765

Ile Ser Arg Leu Tyr Val Pro Leu Tyr Ser Ser Lys Gln Ile Leu Lys
    2770                2775                2780

Gln Lys Leu Leu Leu Ala Ile Lys Thr Lys Asn Phe Gly Phe Val
2785                2790                2795

<210> SEQ ID NO 5
<211> LENGTH: 8493
<212> TYPE: DNA
<213> ORGANISM: Homo sapiens

<400> SEQUENCE: 5
cgccctcgag tggaggacga gaaggaaagc accatgacgt ccatccattt cgtggttcac      60
ccgctgccgg gcaccgagga ccagctcaat gacaggttac gagaagtttc tgagaagctg     120
aacaaatata atttaaacag ccacccccct ttgaatgtat ccaacaggc tactattaaa      180
```

```
cagtgtgtgg tgggaccaaa tcatgctgcc tttcttcttg aggatggtag agtttgcagg      240
attggttttt cagtacagcc agacagattg gaattgggta aacctgataa taatgatggg      300
tcaaagttga acagcaactc gggggcaggg aggacgtcaa ggcctggtag acaagcgac       360
tctccatggt ttctctcagg ttctgagact ctaggcaggc tggcaggcaa caccttagga      420
agccgctgga gttctggagt gggtggaagt ggtggaggat cctctggtag gtcatcagct      480
ggagctcgag attcccgccg gcagactcga gttattcgga caggacggga tcgagggtct      540
gggcttttgg gcagtcagcc ccagccagtt attccagcat ctgtcattcc agaggagctg      600
atttcacagg cccaagttgt tttacaaggc aaatccagaa gtgtcattat tcgagaactt      660
cagagaacaa atcttgatgt gaaccttgct gtaaataatt tacttagccg ggatgatgaa      720
gatggagatg atggggatga tacagccagc gaatcttatt tggctggaga ggatcttatg      780
tctctccttg atgccgacat tcattctgcc cacccaagtg tcattattga tgcagatgcc      840
atgttttctg aagacattag ctattttggt taccttcttt tcgtcgttc atcactttcc      900
aggctaggct catctcgagt tctccttctt cccttagaga gagactctga gctgttgcgt      960
gaacgcgaat ccgttttacg tttacgtgaa cgaaggtggc ttgatggagc ctcatttgat     1020
aatgaaaggg gttctaccaa gcaaggaagg agagccaaac ttgataagaa gaatacacct     1080
gttcaaagtc cagtatctct aggagaagat ttgcagtggt ggcctgataa ggatggaaca     1140
aaattcatct gtatggctct gtattctgaa cttctggctg tcagcagtaa aggagaactt     1200
tatcagtgga aatggagtga atctgagcct tacagaaatg cccagaatcc ttcattacat     1260
catccacgag caacattttt ggggttaacc aatgaaaaga tagtcctcct gtctgcaaat     1320
agcataagag caactgtagc tacagaaaag aacaaggttg ctacatgggt ggatgaaact     1380
ttaagttctg tggcttctaa attagagcac actgctcaga cttactctga acttcaagga     1440
gagcggatag tttctttaca ttgctgtgcc ctttacacct gcgctcagct ggaaaacagt     1500
ttatattggt ggggtgtagt tccttttagt caaaggaaga aaatgttaga gaaagctaga     1560
gcaaaaaata aaaagcctaa atccagtgct ggtatttctt caatgccgaa catcactgtt     1620
ggtacccagg tatgcttgag aaataatcct ctttatcatg ctggagcagt tgcattttca     1680
attagtgctg ggattcctaa agttggtgtc ttaatggagt cagtttggaa tatgaatgac     1740
agctgtagat ttcaacttag atctcctgaa agcttgaaaa acatggaaaa agctagcaaa     1800
actactgaag ctaagcctga aagtaagcag gagccagtga aaacagaaat gggtcctcca     1860
ccatctccag catccacgtg tagtgatgca tcctcaattg ccagcagtgc atcaatgcca     1920
tacaaacgac gacggtcaac ccctgcacca aagaagagg aaaaggtgaa tgaagagcag      1980
tggtctcttc gggaagtggt ttttgtggaa gatgtcaaga atgttcctgt tggcaaggtg     2040
ctaaaagtag atggtgccta tgttgctgta aaatttccag gaacctccag taatactaac     2100
tgtcagaaca gctctggtcc agatgctgac ccttcttctc tcctgcagga ttgtaggtta     2160
cttagaattg atgaattgca ggttgtcaaa actggtggaa caccgaaggt tcccgactgt     2220
ttccaaagga ctcctaaaaa gctttgtata cctgaaaaaa cagaaatatt agcagtgaat     2280
gtagattcca aggtgttca tgctgttctg aagactggaa attgggtgcg atactgtatc     2340
tttgatcttg ctacaggaaa agcagaacag gaaaataatt ttcctacaag cagcattgct     2400
ttccttggtc agaatgagag gaatgtagcc attttcactg ctggacagga atctcccatt     2460
attcttcgag atggaaatgg taccatctac ccaatggcca aagattgcat gggaggaata     2520
```

```
agggatcccg attggctgga tcttccacct attagtagtc ttggaatggg tgtgcattct   2580
ttaataaatc ttcctgccaa ttcaacaatc aaaaagaaag ctgctgttat catcatggct   2640
gtagagaaac aaaccttaat gcaacacatt ctgcgctgtg actatgaggc ctgtcgacaa   2700
tatctaatga atcttgagca acggttttta gagcagaatc tacagatgct gcagacattc   2760
atcagccaca gatgtgatgg aaatcgaaat attttgcatg cttgtgtatc agtttgcttt   2820
ccaaccagca ataaagaaac taagaagaa gaggaagcgg agcgttctga agaaataca    2880 tttgcagaaa ggctttctgc tgttgaggcc attgcaaatg caatatcagt tgtttcaagt   2940 aatgcccag gtaatcgggc tggatcatca agtagccgaa gtttgagatt acgggaaatg    3000
atgagacgtt cgttgagagc agctggtttg ggtagacatg aagctggagc ttcatccagt   3060
gaccaccagg atccagtttc accccccata gctcccccta gttgggttcc tgaccctcct   3120
gcgatggatc ctgatggtga cattgatttt atcctggccc cgctgtggg atctcttacc    3180 acagcagcaa ccggtactgg tcaaggacca agcacctcca ctattccagg tccttccaca   3240
gagccatctg tagtagaatc caaggatcga aaggcgaatg ctcattttat attgaaattg   3300
ttatgtgaca gtgtggttct ccagccctat ctacgagaac ttctttctgc caaggatgca   3360
agagggatga ccccatttat gtcagctgta agtggccgag cttatcctgc tgcaattacc   3420
atcttagaaa ctgctcagaa aattgcaaaa gctgaaatat cctcaagtga aaagaggaa    3480 gatgtattca tgggaatggt ttgcccatca ggtaccaacc ctgatgactc tcctttatat   3540
gttttatgtt gtaatgacac ttgcagtttt acatggactg gagcagagca cattaaccag   3600 gatattttg agtgtcgaac ttgtggcttg ctggagtcac tgtgttgttg tacggaatgt    3660
gcagggtttt gtcataaagg tcatgattgg aaactcaaac ggacatcacc aacagcctac   3720
tgtgactgtt gggagaaatg taaatgtaaa actcttattg ctggacagaa atctgctcgt   3780
cttgatctac tttatcgcct gctcactgct actaatctgg ttactctgcc aaacagcagg   3840
ggagagcacc tcttactatt cttagtacag acagtcgcaa ggcagacggt ggagcattgt   3900
caatacaggc cacctcgaat cagggaagat cgtaaccgaa aaacagccag tcctgaagat   3960
tcagatatgc cagatcatga tttagagcct ccaagatttg cccagcttgc attggagcgt   4020
gttctacagg actggaatgc cttgaaatct atgattatgt ttgggtcgca ggagaataaa   4080
gaccctctta gtgccagcag tagaataggc catcttttgc cagaagagca agtataccctc   4140 aatcagcaaa gtggcacaat tcggctggac tgtttcactc attgccttat agttaagtgt   4200
acagcagata ttttgctttt agatactcta ctaggtacac tagtgaaaga actccaaaac   4260
aaatatacac ctggacgtag agaagaagct attgctgtga caatgaggtt tctacgttca   4320
gtggcaagag ttttttgttat tctgagtgtg gaaatggctt catccaaaaa gaaaacaac    4380 tttattccac agccaattgg aaaatgcaag cgtgtattcc aagcattgct accttacgct   4440
gtggaagaat tgtgcaacgt agcagagtca ctgattgttc ctgtcagaat ggggattgct   4500
cgtccaactg caccatttac cctggctagt actagcatag atgccatgca gggcagtgaa   4560
gaattatttt cagtggaacc actgccacca cgaccatcat ctgatcagtc tagcagctcc   4620
agtcagtctc agtcatccta catcatcagg aatccacagc agaggcgcat cagccagtca   4680
cagcccgttc ggggcagaga tgaagaacag gatgatattg tttcagcaga tgtgaagag    4740 gttgaggtgg tggagggtgt ggctggagaa gaggatcatc atgatgaaca ggaagaacac   4800
ggggaagaaa atgctgaggc agagggacaa catgatgagc atgatgaaga cgggagtgat   4860
atggagctgg acttgttagc agcagcagaa acagaaagtg atagtgaaag taaccacagc   4920
```

```
aaccaagata atgctagtgg gcgcagaagc gttgtcactg cagcaactgc tggttcagaa    4980
gcaggagcaa gcagtgttcc tgccttcttt tctgaagatg attctcaatc gaatgactca    5040
agtgattctg atagcagtag tagtcagagt gacgacatag aacaggagac ctttatgctt    5100
gatgagccat tagaaagaac cacaaatagc tcccatgcca atggtgctgc ccaagctccc    5160
cgttcaatgc agtgggctgt ccgcaacacc ctgcatcagc gagcagccag tacagcccct    5220
tccagtacat ctacaccagc agcaagttca gcgggtttga tttatattga tccttcaaac    5280
ttacgccgga gtggtaccat cagtacaagt gctgcagctg cagcagctgc tttggaagct    5340
agcaacgcca gcagttacct aacatctgca agcagtttag ccagggctta cagcatgtca    5400
ttagacaaat catcggactt gatgggcctt attcctaagt ataatcacct agtatactct    5460
cagattccag cagctgtgaa attgacttac caagatgcag taaacttaca gaactatgta    5520
gaagaaaagc ttattcccac ttggaactgg atggtcagta ttatggattc tactgaagct    5580
caattacgtt atggttctgc attagcatct gctggtgatc ctggacatcc aaatcatcct    5640
cttcacgctt tcagaattc agcgagaaga gagaggatga ctgcgcgaga agaagctagc    5700
ttacgaacac ttgaaggcag acgacgtgcc accttgctta gcgcccgtca aggaatgatg    5760
tctgcacgag gagacttcct aaattatgct ctgtctctaa tgcggtctca taatgatgag    5820
cattctgatg ttcttccagt tttggatgtt tgctcattga agcatgtggc atatgttttt    5880
caagcactta tatactggat taaggcaatg aatcagcaga caacattgga tacacctcaa    5940
ctagaacgca aaaggacgcg agaactcttg gaactgggta ttgataatga agattcagaa    6000
catgaaaatg atgatgacac caatcaaagt gctactttga atgataagga tgatgactct    6060
cttcctgcag aaactggcca aaaccatcca ttttccgac gttcagactc catgacattc    6120
cttgggtgta tacccccaaa tccatttgaa gtgcctctgg ctgaagccat ccccttggct    6180
gatcagccac atctgttgca gccaaatgct agaaaggagg atcttttttgg ccgtccaagt    6240
cagggtcttt attcttcatc tgccagtagt gggaaatgtt taatggaggt tacagtggat    6300
agaaactgcc tagaggttct tccaacaaaa atgtcttatg ctgccaatct gaaaaatgta    6360
atgaacatgc aaaaccggca aaaaaagaag gggaaggaac agcccgtgct gccagaagaa    6420
actgagagtt caaaaccagg gccatctgct catgatcttg ctgcacaatt aaaaagtagc    6480
ttactagcag aaataggact tactgaaagt gaagggccac ctctcacatc tttcaggcca    6540
cagtgtagct ttatgggaat ggttctttcc catgatatgc tgctaggacg ttggcgcctt    6600
tctttagaac tgttcggcag ggtattcatg aagatgttg agcagaacc tggatcaatc    6660
ctaactgaat tgggtggttt tgaggtaaaa gaatcgaaat tccgcagaga aatgaaaaa    6720
ctgagaaacc agcagtcaag agatttgtca ctagaggttg atcgggatcg agatcttctc    6780
attcagcaga ctatgaggca gcttaacaat cactttggtc gaagatgtgc tactatacca    6840
atggctgtac acagagtaaa agtcacattt aaggatgagc caggagaggg cagtggtgta    6900
gcacgaagtt tttatacagc cattgcacaa gcattttat caaatgaaaa attgccaaat    6960
ctagagtgta tccaaaatgc caacaaaggc acccacacaa gtttaatgca gagattaagg    7020
aaccgaggag agagaccg ggaagggag agagaaggg aaatgaggag gagtagtggt    7080
ttgcgagcag gttctcggag ggaccgggat agagacttta agacagct ttccatcgac    7140
actaggccct ttagaccagc ctctgaaggg aatcctagcg atgatcctga gcctttgcca    7200
gcacatcggc aggcacttgg agagaggctt tatcctcgtg tacaagcaat gcaaccagca    7260
```

-continued

```
tttgcaagta aaatcactgg catgttgttg gattatccca gctcagctgc ttctcttcta    7320
gcaagtgagg attctctgag agcaagagtg gatgaggcca tggaactcat tattgcacat    7380
ggacgggaaa atggagctga tagtatcctg gatcttggat tagtagactc ctcagaaaag    7440
gtacagcagg aaaaccgaaa gcgccatggc tctagtcgaa gtgtagtaga tatggattta    7500
gatgatacag atgatggtga tgacaatgcc cctttgtttt accaacctgg gaaaagagga    7560
ttttatactc caaggcctgg caagaacaca gaagcaaggt tgaattgttt cagaaacatt    7620
ggcaggattc ttggactatg tctgttacag aatgaactct gtcctatcac attgaataga    7680
catgtaatta aagtattgct tggtagaaaa gtcaattggc atgattttgc ttttttttgat   7740 cctgtaatgt atgagagttt gcggcaacta atcctcgcgt ctcagagttc agatgctgat    7800
gctgttttct cagcaatgga tttggcattt gcaattgacc tgtgtaaaga agaaggtgga    7860
ggacaggttg aactcattcc taatggtgta aagagaccag tcactccaca gaatgtatat    7920
gagtatgtgc ggaaagacgc agaacacaga atgttggtag ttgcagaaca gcccttacat    7980
gcaatgagga aggtctact agatgtgctt ccaaaaaatt cattagaaga tttaacggca    8040
gaagatttta ggcttttggt aaatggctgc ggtgaagtca atgtgcaaat gctgatcagt    8100
tttacctctt tcaatgatga atcaggagaa aatgctgaga agcttctgca gttcaagcgt    8160
tggttctggt caatagtaga gaagatgagc atgacagaac gacaagatct tgtttacttt    8220
tggacatcaa gcccatcact gccagccagt gaagaaggat tccagcctat gccctcaatc    8280
acaataagac caccagatga ccaacatctt cctactgcaa atacttgcat ttctcgactt    8340
tacgtcccac tctattcctc taaacagatt ctcaaacaga aattgttact cgccattaag    8400
accaagaatt ttggttttgt gtagagtata aaaagtgtgt attgctgtgt aatattacta    8460
gcaaattttg tagatttttt tccatttgtc tat                                 8493
```

```
<210> SEQ ID NO 6
<211> LENGTH: 31
<212> TYPE: DNA
<213> ORGANISM: Artificial Sequence
<220> FEATURE:
<223> OTHER INFORMATION: Differential
      display PCR primer

<400> SEQUENCE: 6
acgactcact atagggcttt tttttttta c                                    31

<210> SEQ ID NO 7
<211> LENGTH: 26
<212> TYPE: DNA
<213> ORGANISM: Artificial Sequence
<220> FEATURE:
<223> OTHER INFORMATION: Differential
      display PCR primer

<400> SEQUENCE: 7
acaatttcac acaggagcta gcagac                                         26

<210> SEQ ID NO 8
<211> LENGTH: 24
<212> TYPE: DNA
<213> ORGANISM: Artificial Sequence
<220> FEATURE:
<223> OTHER INFORMATION: M13 forward primer

<400> SEQUENCE: 8
agcggataac aatttcacac agga                                           24
```

```
<210> SEQ ID NO 9
<211> LENGTH: 20
<212> TYPE: DNA
<213> ORGANISM: Artificial Sequence
<220> FEATURE:
<223> OTHER INFORMATION: T7 promoter primer

<400> SEQUENCE: 9
taatacgact cactataggg                                                 20

<210> SEQ ID NO 10
<211> LENGTH: 19
<212> TYPE: DNA
<213> ORGANISM: Artificial Sequence
<220> FEATURE:
<223> OTHER INFORMATION: SP6 promoter primer

<400> SEQUENCE: 10
gatttaggtg acactatag                                                  19

<210> SEQ ID NO 11
<211> LENGTH: 31
<212> TYPE: DNA
<213> ORGANISM: Rattus rattus

<400> SEQUENCE: 11
gacgaagggc cctgactgcg cgagaagaag c                                    31

<210> SEQ ID NO 12
<211> LENGTH: 30
<212> TYPE: DNA
<213> ORGANISM: Rattus rattus

<400> SEQUENCE: 12
aaagaattct gtcatggagt ctgaacgtcg                                      30

<210> SEQ ID NO 13
<211> LENGTH: 20
<212> TYPE: DNA
<213> ORGANISM: Homo sapiens

<400> SEQUENCE: 13
cacgctccaa tgcaagctgg                                                 20

<210> SEQ ID NO 14
<211> LENGTH: 36
<212> TYPE: DNA
<213> ORGANISM: Artificial Sequence
<220> FEATURE:
<223> OTHER INFORMATION: RACE PCR primer
<220> FEATURE:
<221> NAME/KEY: misc_feature
<222> LOCATION: (1)...(36)
<223> OTHER INFORMATION: n = A,T,C or G

<400> SEQUENCE: 14
ggccacgcgt cgactagtac gggnngggnn gggnng                               36

<210> SEQ ID NO 15
<211> LENGTH: 24
<212> TYPE: DNA
<213> ORGANISM: Homo sapiens

<400> SEQUENCE: 15
```

```
cgatcttccc tgattcgagg tggc                                          24
```

<210> SEQ ID NO 16
<211> LENGTH: 21
<212> TYPE: DNA
<213> ORGANISM: Homo sapiens

<400> SEQUENCE: 16

```
ctgtattgac aatgctccac c                                             21
```

<210> SEQ ID NO 17
<211> LENGTH: 16
<212> TYPE: PRT
<213> ORGANISM: Homo sapiens

<400> SEQUENCE: 17

```
Ser Ser Glu Lys Val Gln Gln Glu Asn Arg Lys Arg His Gly Ser Ser
1               5                   10                  15
```